(12) United States Patent
Takata et al.

(10) Patent No.: US 9,008,390 B2
(45) Date of Patent: Apr. 14, 2015

(54) SIMILAR CASE SEARCHING APPARATUS, RELEVANCE DATABASE GENERATING APPARATUS, SIMILAR CASE SEARCHING METHOD, AND RELEVANCE DATABASE GENERATING METHOD

(71) Applicant: Panasonic Corporation, Osaka (JP)

(72) Inventors: Kazutoyo Takata, Fukui (JP); Kenji Kondo, Kyoto (JP); Kazuki Kozuka, Fukui (JP); Yoshikuni Sato, Fukui (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 14/091,939

(22) Filed: Nov. 27, 2013

(65) Prior Publication Data

US 2014/0089000 A1  Mar. 27, 2014

Related U.S. Application Data

(63) Continuation of application No. PCT/JP2012/001141, filed on Feb. 21, 2012.

(30) Foreign Application Priority Data

Jun. 30, 2011 (JP) .................................. 2011-146698

(51) Int. Cl.
*G06K 9/00* (2006.01)
*G06F 19/00* (2011.01)
(Continued)

(52) U.S. Cl.
CPC ............ *G06F 19/321* (2013.01); *A61B 6/5211* (2013.01); *G06F 19/3443* (2013.01); *G06Q 10/10* (2013.01); *G06Q 50/22* (2013.01); *A61B 6/032* (2013.01)

(58) Field of Classification Search
None
See application file for complete search history.

(56) References Cited

U.S. PATENT DOCUMENTS 8,238,663 B2   8/2012  Kato
8,380,013 B2   2/2013  Hisanaga et al.
(Continued)

FOREIGN PATENT DOCUMENTS

JP   2004-157623   6/2004
JP   2008-52544    3/2008
(Continued)

OTHER PUBLICATIONS

Kamarainen, T. Kauppi1V Kalesnykiene2J-K., et al. "the DIARETDB1 diabetic retinopathy database and evaluation protocol."*

(Continued)

*Primary Examiner* — Stephen R Koziol
*Assistant Examiner* — Raphael Schwartz
(74) *Attorney, Agent, or Firm* — Wenderoth, Lind & Ponack, L.L.P.

(57) ABSTRACT

A similar case searching apparatus includes: a search vector generating unit which: with reference to a relevance database storing the degrees of relevance between (i) a combination of the keyword extracted by the keyword extracting unit and the attribute value of the keyword obtained by the keyword attribute obtaining unit and (ii) the respective image feature quantities extracted by the image feature extracting unit, performs weighting on (i) the image feature quantities extracted by the image feature extracting unit and (ii) image feature quantities extracted from a second medical image group of medical images included in a second case data item stored in the case database, using the degrees of relevance as weights; and a similar case searching unit which searches out, from the case database, the second case data item similar to a first case data item by comparing the weighed image feature quantities (i) and (ii).

19 Claims, 15 Drawing Sheets

(51) Int. Cl.
  *G06Q 10/10* (2012.01)
  *A61B 6/00* (2006.01)
  *G06Q 50/22* (2012.01)
  *A61B 6/03* (2006.01)

(56) References Cited

U.S. PATENT DOCUMENTS

| | | |
|---|---|---|
| 2008/0052126 A1 | 2/2008 | Sasai et al. |
| 2009/0097756 A1 | 4/2009 | Kato |
| 2010/0232661 A1 | 9/2010 | Hisanaga et al. |

FOREIGN PATENT DOCUMENTS

| | | |
|---|---|---|
| JP | 2008-77163 | 4/2008 |
| JP | 2008-79770 | 4/2008 |
| JP | 2009-93563 | 4/2009 |
| JP | 2010-211749 | 9/2010 |
| JP | 2011-118540 | 6/2011 |

OTHER PUBLICATIONS

International Search Report issued May 22, 2012 in International (PCT) Application No. PCT/JP2012/001141.

Nemoto et al., "Improvement of Tumor Detection Performance in Mammograms by Feature Selection from a Large Number of Features and Proposal of Fast Feature Selection Method", IEICE Transactions on Fundamentals of Electronics, Communication and Computer Sciences, vol. J88-D-II, No. 2, Feb. 2005, pp. 416-426, with partial English translation.

Sakashita et al., "A method for extracting multi organs by estimating CT value distributions from four phase 3D abdominal CT images", IEICE Technical Report, vol. 106, No. 145, Jul. 2006, pp. 49-54, with English abstract.

\* cited by examiner

FIG. 3

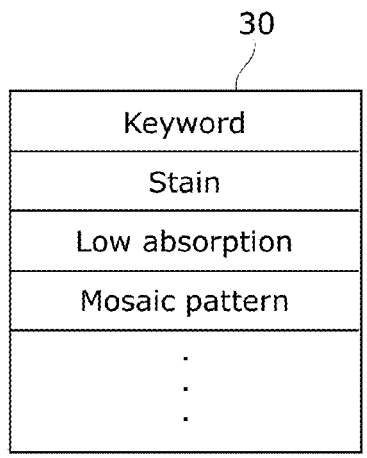

| Keyword |
|---|
| Stain |
| Low absorption |
| Mosaic pattern |
| ... |

FIG. 4

| Attribute | Attribute value | Target word |
|---|---|---|
| Time phase | Simple phase | Simple phase |
| | Arterial phase | Arterial phase, Early phase . . . |
| | Equilibrium phase | Equilibrium phase, Late phase . . . |
| Existence | Existence | Found, Recognized . . . |
| | Non-existence | Not found, Not recognized . . . |
| Portion | Liver | Liver, Liver organ . . . |
| | Liver S1 | Liver segment S1, Liver organ S1 . . . |
| | . . . | . . . |

FIG. 5

| Keyword | Attribute value | | | Degree of relevance with image feature quantity | |
|---|---|---|---|---|---|
| | Time phase | Existence | Portion | Average luminance | Luminance variance |
| Stain | Arterial phase | Existence | Right lobe | 0.8 | 0.2 | ... |
| Stain | Arterial phase | Existence | S1 | 0.8 | 0.2 | ... |
| Stain | Arterial phase | Non-existence | S2 | 0 | 0 | ... |
| Stain | Equilibrium phase | Existence | S3 | 0.2 | 0.8 | ... |
| ... | ... | ... | ... | ... | ... | |

FIG. 8

| Search image | Degree of similarity | Findings |
|---|---|---|
| 1 | 0.8 | Suspicious for Z cancer based on factors A, D, and E |
| 2 | 0.6 | Suspicious for Y cancer based on factors A, B, and D |
| 3 | 0.5 | Suspicious for X cancer based on factors A, B, and D |

Result of similar case search

Result of diagnosis by image interpreter

Findings
Suspicious for X cancer based on factors A, B, and C

| Result of reference case search | | |
|---|---|---|
| X cancer | | |
| Search image | Degree of similarity | Findings |
| | 0.8 | Suspicious for Z cancer based on factors A, D, and E |
| | 0.5 | Suspicious for Z cancer based on factors A, B, and D |
| Y cancer | | |
| Search image | Degree of similarity | Findings |
| | 0.6 | Suspicious for X cancer based on factors A, B, and D |

Result of diagnosis by image interpreter

Findings
Suspicious for X cancer based on factors A, B, and C

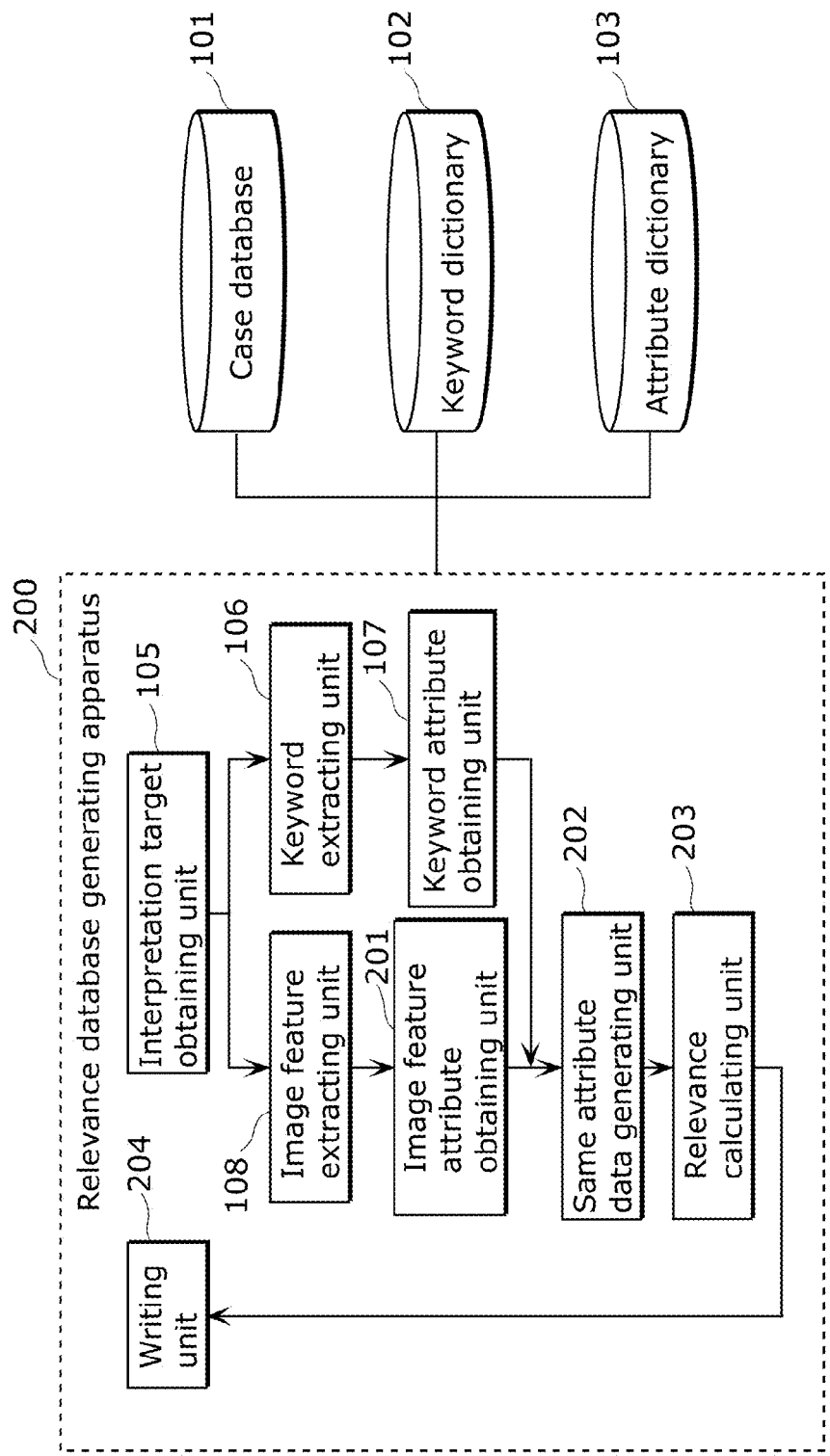

| Attribute | Attribute value | Image capturing time [s] |
|---|---|---|
| Time phase | Simple phase | 0 |
| | Arterial phase | 1 - 80 |
| | Equilibrium phase | 81 or more |

US 9,008,390 B2

SIMILAR CASE SEARCHING APPARATUS, RELEVANCE DATABASE GENERATING APPARATUS, SIMILAR CASE SEARCHING METHOD, AND RELEVANCE DATABASE GENERATING METHOD

CROSS REFERENCE TO RELATED APPLICATIONS

This is a continuation application of PCT International Application No. PCT/JP2012/001141 filed on Feb. 21, 2012, designating the United States of America, which is based on and claims priority of Japanese Patent Application No. 2011-146698 filed on Jun. 30, 2011. The entire disclosures of the above-identified applications, including the specifications, drawings and claims are incorporated herein by reference in their entirety.

FIELD

One or more exemplary embodiments disclosed herein relate to a similar case searching apparatus which automatically presents reference cases for an interpretation target case and a relevance database generating apparatus which generates a relevance database used by the similar case searching apparatus.

BACKGROUND

Recently, in a medical diagnosis field, it is becoming easier for doctors to share a large amount of data with an advancement of digitalization of medical images and image interpretation reports. Here, an image interpretation report is a text data item indicating a diagnosis made by an image interpreter such as a doctor based on a medical image. In addition, image interpretation reports stored in Picture Archiving and Communication Systems (PACS) which are systems for storing and communicating images are managed in an associated manner, and the stored past image interpretation reports are desired to be used secondarily in an effective manner. A method for using such image interpretation reports secondarily is to automatically present reference cases for medical images which are interpretation targets based on which a diagnosis is made. In relation to this, an effort for supporting a decision making related to a diagnosis is expected.

As a conventional technique for realizing presentation of such reference cases, Patent Literature 1 proposes a method of searching out and presenting similar cases using image feature quantities of medical images corresponding to image interpretation reports stored in a database and text information included in the image interpolation reports. More specifically, in the search of the similar cases, a first search is performed to search out image interpretation reports which show similar image forms from among the image interpretation reports. Subsequently, a second search is performed to extract representative keywords between text information items in the image interpretation reports searched out in the first search, select image feature quantities associated in advance with the extracted keywords, and calculate degrees of similarity between the cases based on the selected image feature quantities. The text information items described in the image interpretation report show a viewpoint of the image interpreter. In other words, the method disclosed in Patent Literature 1 makes it possible to present the similar cases searched out based on the viewpoint of the image interpreter, on condition that images and keywords are associated with each other in advance.

CITATION LIST

Patent Literature

[PTL 1]
Japanese Unexamined Patent Application Publication No. 2009-093563

SUMMARY

Technical Problem

However, the method disclosed in Patent Literature 1 does not make it possible to associate image feature quantities and a keyword included in an image interpretation report in which a single image interpretation report is assigned to a plurality of medical images. For this reason, the method has a problem that it is impossible to present similar cases searched out based on a viewpoint of an image interpreter and written in the image interpretation report.

A contrast enhanced Computed Tomography (CT) scan is an example of a diagnosis in which a single image interpretation report is assigned to a plurality of medical images. In the contrast enhanced CT scan, the plurality of images are captured in time periods before and after an administration of a contrast medium to a patient. An image interpreter or a doctor watches the captured images to check a temporal transition of contrast enhancement effects, to generate the image interpretation report.

The image interpretation report generated in this way includes a keyword assigned to all the images and a keyword assigned to particular one or more of the images. More specifically, a keyword related to a disease name such as "hepatocellular carcinoma" is a keyword assigned to all the captured images. On the other hand, a keyword related to image findings, for example "stain" or "low absorption" is a keyword assigned to specific one or more of the images. These keywords are written in the image interpretation report in a mixed manner, and thus it is impossible to simply associate the keyword and the medical images.

As described above, the text information item described in the image interpretation report shows the viewpoint of the image interpreter. In other words, when the keyword and the medical images are associated mistakenly, it is impossible to present any similar case searched out based on the viewpoint of the image interpreter.

In view of this, one non-limiting and exemplary embodiment provides a similar case searching apparatus and a similar case searching method which make it possible to search out similar cases based on a viewpoint of an image interpreter (hereinafter also referred to as a user) such as a doctor in a userfriendly manner, even when a single image interpretation report is assigned to a plurality of medical images.

Furthermore, non-limiting and exemplary embodiments provide a relevance database generating apparatus and a relevance database generating method which make it possible to generate a relevance database which is used by the similar case searching apparatus.

Solution to Problem

In one general aspect, the apparatus disclosed here features a similar case searching apparatus which searches out, from a case database, at least one second case data item similar to a first case data item including a first medical image group of first medical images and a first image interpretation report which is a text data item indicating a result of interpreting the first medical image group, the similar case searching apparatus including: an image feature extracting unit configured to extract a plurality of image feature quantities from the first medical image group; a keyword extracting unit configured to extract a keyword from the first image interpretation report, the keyword being either (a) an image interpretation item which is a character string indicating a feature of at least one of the first medical images or (b) a disease name which is a result of a diagnosis made by a user based on the first medical images; a keyword attribute obtaining unit configured to obtain an attribute value which is a word indicating a supplemental concept of the keyword, from a sentence including the keyword extracted by the keyword extracting unit; a search vector generating unit configured to: with reference to a relevance database storing the degrees of relevance between (i) a combination of the keyword extracted by the keyword extracting unit and the attribute value of the keyword obtained by the keyword attribute obtaining unit and (ii) the respective image feature quantities extracted by the image feature extracting unit, perform weighting on (i) the image feature quantities extracted by the image feature extracting unit and (ii) image feature quantities extracted from a second medical image group of second medical images included in the at least one second case data item stored in the case database, using the degrees of relevance as weights; and generate a search vector for the first medical image group and a search vector for the second medical image group, each of the search vectors having, as elements, corresponding ones of image feature quantities resulting from the weighting; and a similar case searching unit configured to search out the at least one second case data item stored in the case database, based on a degree of similarity between the search vector for the first medical image group and the search vector for the second medical group.

These general and specific aspects may be implemented using a system, a method, an integrated circuit, a computer program, or a computer-readable recording medium such as a computer-readable CD-ROM, or any combination of systems, methods, integrated circuits, computer programs, or computer-readable recording media.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

The similar case searching apparatus according to one or more exemplary embodiments or features disclosed herein is capable of searching out similar cases based on a viewpoint of an image interpreter in a userfriendly manner, even when a single image interpretation report is assigned to a plurality of medical images.

BRIEF DESCRIPTION OF DRAWINGS

These and other advantages and features will become apparent from the following description thereof taken in conjunction with the accompanying Drawings, by way of non-limiting examples of embodiments disclosed herein.

FIG. 3 is a diagram showing an example of a keyword dictionary.

FIG. 4 is a diagram showing an example of an attribute dictionary.

FIG. 5 is a diagram showing an example of a relevance database.

FIG. 8 is a diagram showing an example of a display screen output onto the output medium by the output unit.

FIG. 9 is a diagram showing an example of a display screen output onto the output medium by the output unit.

FIG. 10 is a block diagram showing a functional structure of a relevance database generating apparatus according to Embodiment 2.

DESCRIPTION OF EMBODIMENTS

Figure 1:
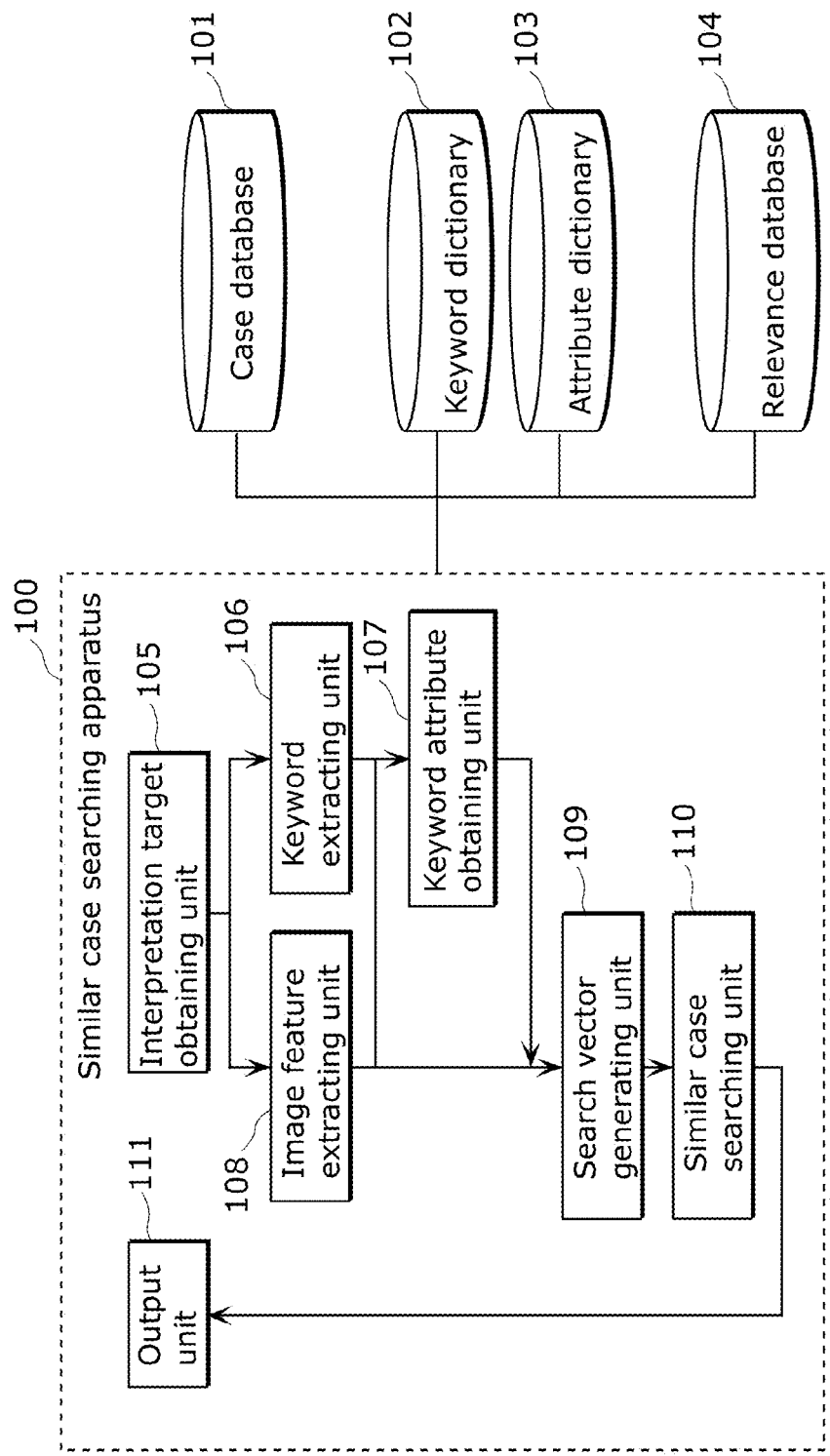
FIG. 1 is a block diagram showing a functional structure of a similar case searching apparatus according to Embodiment 1.

Hereinafter, embodiments are described in detail with reference to the drawings. It is to be noted that each of the embodiments described below is a non-limiting general or specific example. The numerical values, structural elements, the arrangement and connection of the structural elements, steps, the processing order of the steps etc. shown in the following exemplary embodiments are mere examples, and therefore do not limit the scope of the Claims. Therefore, among the structural elements in the following exemplary embodiment, structural elements not recited in any one of the independent claims which define the generic concept of the present disclosure are described as arbitrary structural elements.

The similar case searching apparatus according to an embodiment of the present disclosure is intended to search out similar cases for a case presented by medical images interpreted by an image interpreter. The medical images are, for example, ultrasonic images, CT images, or nuclear magnetic resonance images.

In one general aspect, the apparatus disclosed here features a similar case searching apparatus which searches out, from a case database, at least one second case data item similar to a first case data item including a first medical image group of first medical images and a first image interpretation report which is a text data item indicating a result of interpreting the first medical image group, the similar case searching apparatus including: an image feature extracting unit configured to extract a plurality of image feature quantities from the first medical image group; a keyword extracting unit configured to extract a keyword from the first image interpretation report, the keyword being either (a) an image interpretation item which is a character string indicating a feature of at least one of the first medical images or (b) a disease name which is a result of a diagnosis made by a user based on the first medical images; a keyword attribute obtaining unit configured to obtain an attribute value which is a word indicating a supplemental concept of the keyword, from a sentence including the keyword extracted by the keyword extracting unit; a search vector generating unit configured to: with reference to a relevance database storing the degrees of relevance between (i) a combination of the keyword extracted by the keyword extracting unit and the attribute value of the keyword obtained by the keyword attribute obtaining unit and (ii) the respective image feature quantities extracted by the image feature extracting unit, perform weighting on (i) the image feature quantities extracted by the image feature extracting unit and (ii) image feature quantities extracted from a second medical image group of second medical images included in the at least one second case data item stored in the case database, using the degrees of relevance as weights; and generate a search vector for the first medical image group and a search vector for the second medical image group, each of the search vectors having, as elements, corresponding ones of image feature quantities resulting from the weighting; and a similar case searching unit configured to search out the at least one second case data item stored in the case database, based on a degree of similarity between the search vector for the first medical image group and the search vector for the second medical group.

With this structure, weighting is performed on the image feature quantities in the generation of the search vectors. At this time, the weights used in the weighting are (i) combinations of a keyword extracted from the first image interpretation report and an attribute value for the keyword, and (ii) the degrees of relevance with image feature quantities. The keyword and attribute value are values indicating a viewpoint of the image interpreter. For this reason, it is possible to search out the similar cases based on the viewpoint of the image interpreter. In addition, the attribute value indicates a supplemental concept of the keyword. For this reason, the attribute value is a clue for finding out which one of the first medical images in the first medical image group was used as a basis of the image interpretation report. Thus, it is possible to search out the similar cases based on the viewpoint of the image interpreter, even for the case including the plurality of medical images and the single image interpretation report assigned to the medical images.

For example, the keyword attribute obtaining unit may be configured to obtain, as the attribute value of the keyword, a time phase attribute value indicating a relative image capturing time of a corresponding one of the first medical images in the first medical image group or a relative image capturing time period in which the corresponding first medical image is captured, from the sentence including the keyword extracted by the keyword extracting unit.

The use of the time phase attribute value as the attribute value makes it possible to find out which one of the first medical images in the first medical image group was used as a basis of the image interpretation report. For this reason, it is possible to search out the similar cases based on the viewpoint of the image interpreter, even for the case including the plurality of medical images and the single image interpretation report assigned to the first medical image group.

For example, the keyword attribute obtaining unit may be configured to obtain, as the attribute value of the keyword, an existence attribute value indicating existence or non-existence of information in the at least one of the first medical images, from the sentence including the keyword indicating the information and extracted by the keyword extracting unit.

When one of the first medical images includes information indicated by an image interpretation item but another one of the first medical images does not include information indicated by an image interpretation item, the use of the existence attribute value as the attribute value makes it possible to find out which one of the first medical images in the first medical image group was used as a basis of the image interpretation report. For this reason, it is possible to search out the similar cases based on the viewpoint of the image interpreter, even for the case including the plurality of medical images and the single image interpretation report assigned to the first medical image group.

For example, the keyword attribute obtaining unit may be configured to obtain, as the attribute value of the keyword, a portion attribute value indicating a portion of an organ whose image is to be interpreted, from the sentence including the keyword extracted by the keyword extracting unit.

When first medical images to be interpreted show different portions of an organ, the use of the portion attribute value as the attribute value makes it possible to find out which one of the first medical images in the first medical image group was used as a basis of the image interpretation report. For this reason, it is possible to search out the similar cases based on the viewpoint of the image interpreter, even for the case including the plurality of medical images and the single image interpretation report assigned to the first medical image group.

For example, the similar case searching apparatus may further include an output unit configured to output the at least one second case data item searched out by the similar case searching unit to outside the similar case searching apparatus.

For example, the output unit may be configured to classify each of the at least one second case data item searched out by the similar case searching unit into a corresponding one of case data item groups each based on similar diseases names, and output the classified at least one second case data item to outside the similar case searching apparatus.

The image interpreter needs to find out, using the results of searching the similar cases, a disease name description different from the diagnosis by himself or herself from the findings in the search results when considering a possibility of a disease other than the disease as the result of the diagnosis (image interpretation) by himself or herself. By presenting the search results for each of case data item groups each classified based on similar diseases names, the image interpreter can easily check the disease names in the cases presented as the search results, and can reduce image interpretation time.

For example, the similar case searching unit may be configured to search for only one or more second case data items each assigned with an image interpretation report in which an image finding and a definitive diagnosis match from among second case data items stored in the case database, the image finding may be a result of a diagnosis made by an image interpreter based on the second medical image group included in the second case data item, and the definitive diagnosis may be a final diagnosis result obtained based on the second medical image group included in the second case data item.

The image findings are results of a diagnosis by the image interpreter on the first medical images included in the case data item, and the definitive diagnosis is the final diagnosis result on the first medial images included in the case data item. The case database includes the medical images based only on which it is impossible to indicate a lesion that matches the definitive diagnosis, due to image noise or characteristics of an imaging device. There is a high possibility that it is difficult to estimate a lesion based only on such medical images. Thus, presentation of such a similar case data item may increase the risk of a misdiagnosis. In contrast, each of case data items in which image findings and a definitive diagnosis match is a case data item which guarantees that it is possible to point out the same lesion as the lesion in the definitive diagnosis from the medical images. Thus, the case data item is appropriate as a similar case data item. Thus, by determining, as the search targets, only the case data items in each of which image findings and a definitive diagnosis match, it is possible to reduce the risk of a misdiagnosis made with reference to similar cases.

In one general aspect, the apparatus disclosed here features a relevance database generating apparatus, including: an image feature extracting unit configured to extract image feature quantities from a plurality of medical images; an image feature attribute obtaining unit configured to obtain attribute values of the respective image feature quantities extracted by the image feature extracting unit, from the plurality of medical images; a keyword extracting unit configured to extract, as a keyword, either an image interpretation item or a disease name, from an image interpretation report which is a text data item describing a result of interpretation of the medical images by a user, the image interpretation item being a character string indicating a feature of at least one of the medical images, and the disease name being a result of a diagnosis made by the user based on the medical images; a keyword attribute obtaining unit configured to obtain an attribute value of the keyword, from a sentence including the keyword extracted by the keyword extracting unit; a same attribute data generating unit configured to generate a combination of the keyword and each of image feature quantities both having a same attribute value, based on (i) the keyword and the attribute value of the keyword extracted from the image interpretation report and (ii) the image feature quantities extracted from the medical images and the attribute values of the respective image feature quantities; and a relevance calculating unit configured to calculate, from the combination of the keyword and each of the image feature quantities both having the same attribute value, a degree of relevance between the keyword and the image feature quantity, and generate a relevance database indicating a degree of relevance between (i) the combination of the keyword and the attribute value of the keyword and (ii) the image feature quantity.

With this structure, the degrees of relevance are calculated between the keyword and image feature quantities having the same attribute value. For this reason, it is possible to generate the relevance database which (i) stores degrees of relevance between combinations of keywords and attribute values thereof and image feature quantities and (ii) is for use by the aforementioned similar case searching apparatus.

For example, the keyword attribute obtaining unit may be configured to obtain, as the attribute value of the keyword, a time phase attribute value indicating a relative image capturing time of a corresponding one of the medical images or a relative image capturing time period in which the corresponding medical image is captured, from the sentence including the keyword extracted by the keyword extracting unit.

The use of the time phase attribute value as the attribute value makes it possible to generate the relevance database with reference to which it is possible to find out which one of the medical images in the medical image group was used as a basis of the image interpretation report. For this reason, the similar case searching apparatus can search out the similar cases based on the viewpoint of the image interpreter, even for the case including the plurality of medical images and the single image interpretation report assigned to the medical images.

For example, the keyword attribute obtaining unit may be configured to obtain, as the attribute value of the keyword, an existence attribute value indicating existence or non-existence of information shown by the keyword, from the sentence including the keyword, the keyword indicating the feature of the at least one of the medical images and extracted by the keyword extracting unit.

When one of medical images includes information indicated by an image interpretation item but another one of the medical images does not include information indicated by an image interpretation item, the use of the existence attribute value as the attribute value makes it possible to generate the relevance database with reference to which it is possible to find out which one of the medical images was used as a basis of the image interpretation report. For this reason, the similar case searching apparatus can search out the similar cases based on the viewpoint of the image interpreter, even for the case including the plurality of medical images and the single image interpretation report assigned to the medical images.

For example, the keyword attribute obtaining unit may be configured to obtain, as the attribute value of the keyword, a portion attribute value indicating a portion of an organ whose image is to be interpreted, from the sentence including the keyword extracted by the keyword extracting unit.

When medical images to be interpreted show different portions of an organ, the use of the portion attribute value as the attribute value makes it possible to generate the relevance database with reference to which it is possible to find out which one of the medical images was used as a basis of the image interpretation report. For this reason, the similar case searching apparatus can search out the similar cases based on the viewpoint of the image interpreter, even for the case including the plurality of medical images and the single image interpretation report assigned to the medical images.

As a specific example, the image feature attribute obtaining unit may be configured to obtain time phase attribute values as the attribute values of the respective image feature quantities extracted by the image feature extracting unit, from image capturing times of the respective medical images, with reference to a data table in which the image capturing times of the medical images and the time phase attribute values are associated with each other.

For example, the relevance database generating apparatus may further include an interpretation target obtaining unit configured to obtain a plurality of medical images and an image interpolation report corresponding to the medical images included in a case data item, from a case database storing the case data item; and an update control unit configured to cause the interpretation target obtaining unit to obtain, at the time of update of the case database, the medical images and the image interpretation report stored in the case database, wherein the image feature extracting unit may be configured to extract image feature quantities from the medical images obtained by the interpretation target obtaining unit, and the keyword extracting unit may be configured to extract the keyword from the image interpretation report obtained by the interpretation target obtaining unit.

With this structure, when the case database is updated, the medical images and image interpretation report are obtained from the case database. In response to this update, the relevance database storing the degrees of relevance between combinations of keywords and attribute values thereof and image feature quantities is also updated. Thus, the similar case searching apparatus can search out the similar cases based on the viewpoint of the image interpreter.

For example, the update control unit may be configured to cause the interpretation target obtaining unit to obtain, at the time of the update of the case database, medical images and image interpretation reports included in all case data items included in the case database.

For example, the update control unit may be configured to cause the interpretation target obtaining unit to obtain, at the time of the update of the case database, (i) one or more image interpretation reports each including a keyword having an appearance frequency no more than a threshold value among all image interpretation reports stored in the case database and (ii) medical images corresponding to the one or more image interpretation reports.

In the case of a keyword having a low appearance frequency, the uncertainty of the degree of relevance is high, and thus the necessity of updating the degree of relevance is high. In this way, by determining whether or not update is allowed according to the appearance frequency of each keyword in the case database, it is possible to reduce the calculation amount at the time of update, and to thereby reduce the update time.

Embodiment 1

First, terms used in Embodiments 1 to 3 are described.

The "image feature quantities" are extracted from medical image, and relate to, for example, the shapes of organs or lesion portions in the medical images, or the luminance distributions of the medical images. For example, Non-patent Literature describes the use of four hundred and ninety kinds of feature quantities (Non-patent Literature 2: "Improvement of Tumor Detection Performance in Mammograms by Feature Selection from a Large Number of Features and Proposal of Fast Feature Selection Method", by Nemoto, Shimizu, Hagihara, Kobatake, and Nawano, The Journal of the Institute of Electronics, Information and Communication Engineers (J. IEICE) D-II, Vol. J88-D-II, No, 2, pp. 416-426, February 2005). As image feature quantities used in this embodiment, several ten to several hundred kinds of image feature quantities are predefined for each of medical image capturing apparatuses (modality apparatuses) used to capture the medical images or each of target organs used for image interpretation.

A "Keyword" shows any one of an "image interpretation item" and a "disease name" described below.

An "image interpretation item" is defined in this Description as a "character string made by an image interpreter (such as a doctor) as verbally indicating a feature of a interpretation-target medical image". Terms that are used as image interpretation items are limited within certain ranges for the respective medical image capturing apparatuses, target organs, or the like. Examples of the image interpretation items include: Lobular, Spinal, Irregular, Clear border, Unclear contour, Low density, High density, Low absorption, High absorption, Ground-glass opacity, Calcification, Mosaic pattern, Early stain, Low echo, High echo, and Fuzz.

A "disease name" is the name of a disease diagnosed by the image interpreter (such as the doctor) based on medical images and other medical tests. Examples of disease names include hepatocellular carcinoma, cyst, angioma, and so on.

An "attribute" is a word showing a supplemental concept of a keyword. More specifically, attributes are classified into three kinds of time phase attribute, existence attribute, and portion attribute. It is to be noted that an "attribute" is also obtained from an image feature quantity.

A time phase attribute is a concept associated with image capturing time by a test device, or time from when a contrast medium is infused to when image capturing is performed (or to image capturing timing). For example, in the case of a dynamic CT scan using a contrast medium, either an arterial phase, an equilibrium phase, or the like corresponds to the attribute value of a time phase attribute. In other words, a time phase attribute value indicates a relative image capturing time of a corresponding one of the plurality of medical images or a relative image capturing time period in which the corresponding medical image is captured.

An existence attribute is a concept showing whether or not an image interpretation item or a disease name exists or not. The attribute values of existence attributes correspond to "existence" and "non-existence". For example, a sentence that "A stain is recognized" means that a keyword of "stain" "exists", and "is recognized" is a character string information item indicating the attribute value of "existence". In addition, a sentence that "A stain is not recognized" means that a keyword of "stain" does not "exist", and "is not recognized" is a character string information item indicating the attribute value of "non-existence".

A portion attribute is a concept indicating an organ, the position of the organ, or a partial area of the organ. For example, a "liver" or a "liver S1 segment" corresponds to the attribute value of a portion attribute.

Embodiment 1

Explanation of Structure

Hereinafter, a similar case searching apparatus according to Embodiment 1 is described in detail with reference to the drawings.

FIG. 1 is a block diagram showing a functional structure of the similar case searching apparatus according to Embodiment 1.

The similar case searching apparatus 100 is configured to search out case data items (hereinafter also referred to as "cases") according to results of image interpretation by an image interpreter.

The similar case searching apparatus 100 includes: an interpretation target obtaining unit 105; a keyword extracting unit 106; a keyword attribute obtaining unit 107; an image feature extracting unit 108; a search vector generating unit 109; a similar case searching unit 110; and an output unit 111. The similar case searching apparatus 100 is connected to a case database 101, a keyword dictionary 102, an attribute dictionary 103, and a relevance database 104 which are located externally.

Hereinafter, detailed descriptions are sequentially given of structural elements of the case database 101 and the similar case searching apparatus 100 shown in FIG. 1.

The case database 101 is stored in a storage device including a hard disk, a memory, or the like. The case database 101 is a database storing a plurality of case data items each including a plurality of medical images showing images of an interpretation target to be presented to an image interpreter and a single image interpretation report corresponding to the plurality of medical images. Here, the plurality of medical images are image data items used for an image-based diagnosis, and are stored in an electronic medium. In this Description, the image data items may be simply referred to as images. In addition, the image interpretation report is information indicating a result of interpreting the medical images and a definitive diagnosis resulting from a biopsy performed after the image-based diagnosis. The image interpretation report is document data (text data). A biopsy is a medical test which is performed using a microscope or the like to examine an extracted part of a lesion.

Figure 2:
FIG. 2 is a diagram showing an example of a case data item stored in a case database.

FIG. 2 shows exemplary CT images as a medical image group 20 and an exemplary image interpretation report 21 which are included in case data items stored in the case database 101. The medical image group 20 is composed of a plurality of medical images. The image interpretation report 21 includes an image interpretation report ID 22, an image ID 23, image findings 24, and a definitive diagnosis 25.

The image interpretation report ID 22 is an identifier for identifying the image interpretation report 21. The image ID 23 is an identifier for identifying the medical image group 20. The image findings 24 is information indicating a result of diagnosis based on the medical image group 20 having the image ID 23. In other words, the image findings 24 is information indicating the result of the diagnosis (image interpretation result) and a basis for the diagnosis (a basis for the image interpretation), including image interpretation items and a disease name. The definitive diagnosis 25 shows a definitive diagnosis for a patient indicated by the image interpretation report ID 22. Here, the definitive diagnosis is the final diagnosis result clearly showing the real state of the disease of the target patient by performing the pathological test using a microscope onto the test body obtained in a surgery or a biopsy or through other various kinds of means.

The keyword dictionary 102 is stored in, for example, a storage device including a hard disk, a memory, or the like. The keyword dictionary 102 is a database storing keywords extracted from the image interpretation reports 21. FIG. 3 is a diagram showing an example of the keyword dictionary 102. As shown in FIG. 3, the keyword dictionary 102 stores keywords 30 in a list form.

The attribute dictionary 103 is stored in, for example, a storage device including a hard disk, a memory, or the like. The attribute dictionary 103 is a database storing attribute values and target words with the attribute values extracted from the image interpretation reports 21. FIG. 4 is a diagram showing an example of the attribute dictionary 103. As shown in FIG. 4, the attribute dictionary 103 stores predetermined attributes 40 and target words 42 corresponding to the attribute values 41 in an associated form. For example, the attribute values of time phase attributes indicating the image capturing times of the respective medical images included in the medical image group 20 are a simple phase, an arterial phase, and an equilibrium phase. When one of the image interpretation reports 21 includes a word that is an arterial phase or an early phase, the attribute value of the time phase attribute is the arterial phase. When one of the image interpretation reports 21 includes a word that is an equilibrium phase or a late phase, the attribute value of the time phase attribute is the equilibrium phase.

The relevance database 104 is stored in a storage device including a hard disk, a memory, or the like.

The relevance database 104 is a database storing keywords and attributes extracted from image interpretation reports 21 and image feature quantities and degrees of relevance extracted from medical image groups 20. FIG. 5 is a diagram showing an example of the relevance database 104. As shown in FIG. 5, the relevance database 104 stores combinations of keywords 50 and attribute values 51 extracted from one of the current image interpretation reports 21 and degrees of relevance with image feature quantities 52. A larger degree of relevance shows a higher relevance between the both.

The interpretation target obtaining unit 105 obtains, from the case database 101, one of the medical image groups 20 which was used by an image interpreter when making a diagnosis and the image interpretation report 21. For example, information input through a keyboard, a mouse, or the like is stored in a memory or the like. Next, the interpretation target obtaining unit 105 outputs the obtained medical image group 20 and image interpretation report 21 to the keyword extracting unit 106 and the image feature extracting unit 108.

The keyword extracting unit 106 extracts, with reference to the keyword dictionary 102, keywords from the image interpretation report 21 obtained by the interpretation target obtaining unit 105, and outputs the extracted keywords and image interpretation report 21 to the keyword attribute obtaining unit 107. A specific keyword extracting method is described later.

The keyword attribute obtaining unit 107 obtains the attribute values of the respective keywords, using the keywords and image interpretation report 21 obtained from the keyword extracting unit 106 and the attribute dictionary 103, and outputs the obtained combinations of keywords and attribute values to the search vector generating unit 109. A specific keyword attribute value obtaining method is described later.

The image feature extracting unit 108 calculates image feature quantities for the medical image group 20 obtained by the interpretation target obtaining unit 105, and outputs the calculated image feature quantities to the search vector generating unit 109. A specific image feature quantity calculating method is described later.

The search vector generating unit 109 generates a search vector using the combinations of keywords and attribute values obtained from the keyword attribute obtaining unit 107, the image feature quantities obtained from the image feature extracting unit 108, and the relevance database 104. The search vector generating unit 109 outputs the generated search vector to the similar case searching unit 110. Here, a search vector is a vector having, as an element, an image feature quantity for which weighting is performed using a degree of relevance of an image feature quantity shown in the relevance database 104. A specific search vector generating method is described later. It is to be noted that a search vector is generated for each of a first medical image group of first medical images in a case (a first case) which is an interpretation target and each of second medical image groups of second medical images in cases (second cases) stored in the case database 101.

The similar case searching unit 110 searches out a second case having a high degree of relevance with the first case as the interpretation target, from among the cases stored in the case database 101, using the search vectors obtained from the search vector generating unit 109. The similar case searching unit 110 outputs the image interpretation report ID 22 of the searched-out second case to the output unit 111. A specific image similarity calculating method is described later.

The output unit 111 outputs the image interpretation report ID obtained from the similar case searching unit 110 to an output-destination medium located externally. The output-destination medium is, for example, a monitor such as a liquid crystal display and a CRT. The image interpreter can check the case data item when the case data item is output to the output-destination medium.

Next, descriptions are given of operations performed by the similar case searching apparatus 100 configured as described above.

Embodiment 1

Explanation of Operations

Figure 6:
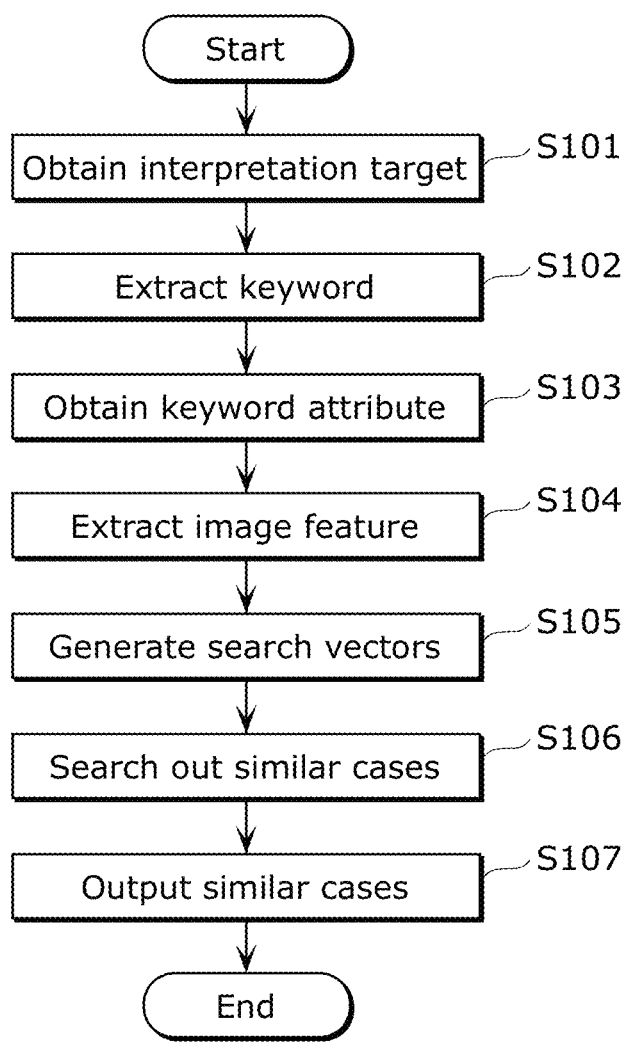
FIG. 6 is a flowchart of overall processes performed by the similar case searching apparatus according to Embodiment 1.

FIG. 6 is a flowchart of overall processes performed by the similar case searching apparatus 100.

First, the interpretation target obtaining unit 105 obtains a first medical image group of first medical images which are interpretation targets and a first image interpretation report which is an image interpretation report for the first medical image group. In other words, the interpretation target obtaining unit 105 obtains, from the case database 101, the medical image group 20 and the image interpretation report 21 used by the image interpreter when the diagnosis was made, as the first medical image group and the first image interpretation report. The interpretation target obtaining unit 105 outputs the obtained medical image group 20 (first medical image group) and the image interpretation report 21 (first image interpretation report) to the image feature extracting unit 108 and the keyword extracting unit 106 (Step S101).

It is good that the medical image group 20 and the image interpretation report 21 are obtained after the completion of the diagnosis by the image interpreter. In this way, the image interpreter can automatically check similar cases after the completion of the diagnosis.

In addition, the interpretation target obtaining unit 105 may obtain the medical image group 20 and the image interpretation report 21 of an arbitrary case selected by the image interpreter even if the case is the one diagnosed by a person other than the image interpreter as long as the case has been already stored in the case database 101. In this way, it is possible to search out the similar cases from among the cases diagnosed by the persons other than the user, and to thereby use them for example, in occasions such as in a conference other than the time of image interpretation.

Next, the keyword extracting unit 106 extracts keywords from the image interpretation report 21 obtained from the interpretation target obtaining unit 105, with reference to the keyword dictionary 102, and outputs the extracted keywords and the image interpretation report 21 to the keyword attribute obtaining unit 107 (Step S102). For example, when a word "stain" is included in the image interpretation report 21, the keyword extracting unit 106 extracts the "stain" as a keyword, with reference to the keyword dictionary 102 shown in FIG. 3.

Next, the keyword attribute obtaining unit 107 obtains the attribute value of each of the keywords, using the keywords and image interpretation report 21 obtained from the keyword extracting unit 106 and the attribute dictionary 103. The keyword attribute obtaining unit 107 outputs the combinations of the keyword and the attribute value to the search vector generating unit 109 (Step S103).

Figure 7:
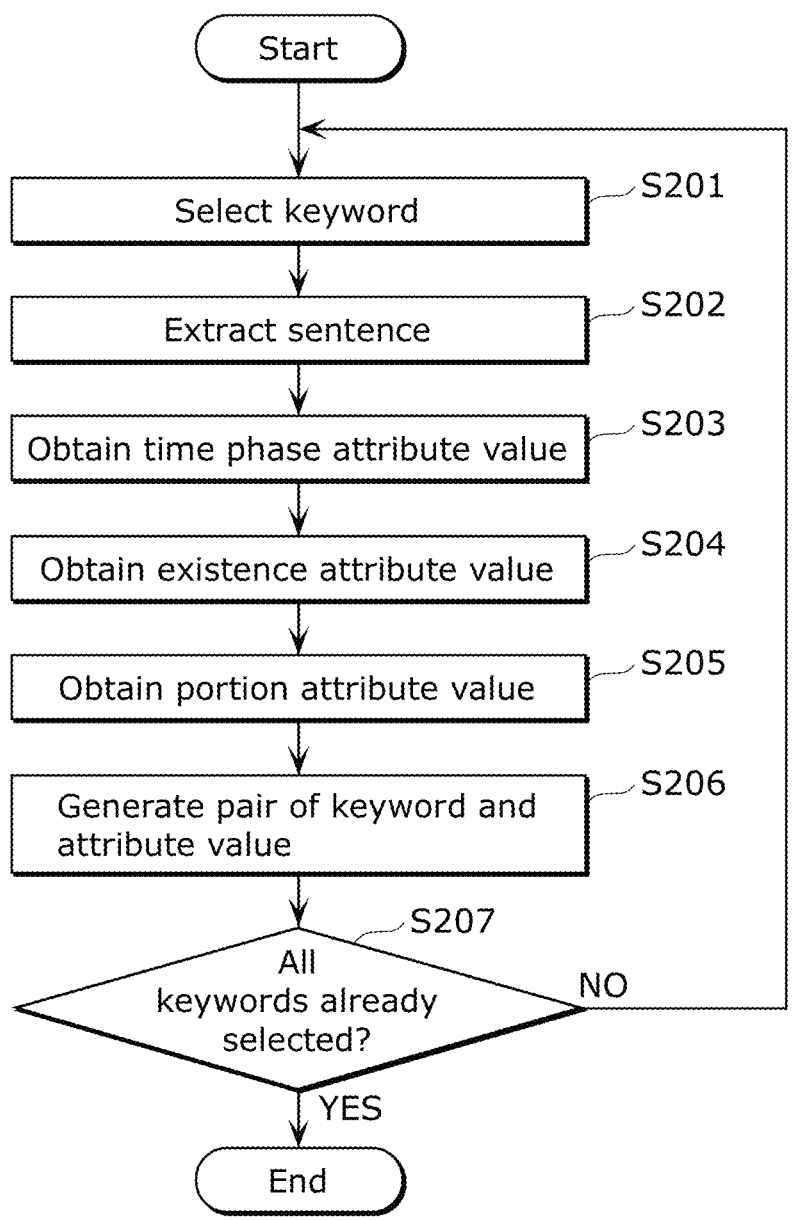
FIG. 7 is a flowchart of detailed processes of a keyword attribute obtainment process (Step S103 in FIG. 6).

FIG. 7 is a flowchart of detailed processes of a keyword attribute obtainment process (Step S103 in FIG. 6).

First, the keyword attribute obtaining unit 107 selects one keyword from among the keywords obtained from the keyword extracting unit 106 (Step S201).

Next, the keyword attribute obtaining unit 107 extracts the sentence including the keyword selected in Step S201 from the image interpretation report 21 obtained from the keyword extracting unit 106 (Step S202). As an exemplary specific sentence extraction process, it is good to extract punctuations etc. such as "line feed marks" and "periods" located before and after the selected keyword, and extract text between the extracted "line feed marks" or "periods" as a sentence.

Next, the keyword attribute obtaining unit 107 obtains the time phase attribute value of the keyword selected in Step S201 from the sentence extracted in Step S202 (Step S203). More specifically, with reference to the attribute dictionary 103, the keyword attribute obtaining unit 107 extracts a target word with a time phase attribute from the sentence extracted in Step S202 and obtains the value of the time phase attribute corresponding to the extracted target word. For example, when the sentence includes a word such as an arterial phase or an early phase, the keyword attribute obtaining unit 107 obtains the arterial phase as the time phase attribute value when extracting the time phase attribute value using the attribute dictionary 103 shown in FIG. 4.

Here, when the keyword extracted by the keyword extracting unit 106 relates to a disease name, it is also good to assign all of time phases as attributes. The disease name is obviously a keyword determined based on information about all the medical images, and thus it is possible to prevent an incorrect attribute from being assigned.

Next, the keyword attribute obtaining unit 107 obtains an existence attribute value of the keyword selected in Step S201 from the sentence extracted in Step S202 (Step S204). More specifically, with reference to the attribute dictionary 103, the keyword attribute obtaining unit 107 extracts a target word with the existence attribute from the sentence extracted in Step S202 and obtains the value of the existence attribute corresponding to the extracted target word.

When the target word with the existence attribute is not included in the sentence, it is only necessary to assign an attribute value "existence" to the keyword selected in Step S201. The image interpretation report includes many incomplete sentences without verbs. For example, a description "Stain in liver S1 segment" is written only when the stain "exists", and therefore "found" or "recognized" explicitly indicating the existence is omitted. When no stain exists, a word with the non-existence is added thereto. An exemplary description "No stain in liver S1 segment" is written. Thus, when a current sentence does not include any word with the non-existence, it is only necessary to assign an attribute value "existence" to the keyword selected in Step S201.

Next, the keyword attribute obtaining unit 107 obtains a portion attribute value of the keyword selected in Step S201 from the sentence extracted in Step S202 (Step S205). More specifically, with reference to the attribute dictionary 103, the keyword attribute obtaining unit 107 extracts a target word with a portion attribute from the sentence extracted in Step S202, and obtains the value of the portion attribute corresponding to the extracted target word (Step S205).

When the sentence does not include any word with the portion attribute, for example, it is also good to sequentially search for sentences before the keyword selected in Step S201, and obtain the portion attribute value searched out initially as the portion attribute value. For example, in the sentences of "A stain is recognized in an early phase of liver segment S1. Washout in a late phase", the keyword "washout" does not have any portion attribute value. However, since the previous sentence has a portion attribute value "liver segment S1", it is possible to assign the portion attribute value to "washout".

In addition, when a current sentence does not include any word with a portion attribute, for example, it is good to select a paragraph including the keyword selected in Step S201 and obtain, as the portion attribute value of the selected keyword, the portion attribute value which has the highest appearance frequency in the selected paragraph. In general, in the image interpretation report written for a plurality of organs, findings regarding each organ are written on a paragraph basis. Since the portion attribute value which has the highest appearance frequency in the selected paragraph is the corresponding organ, it is possible to obtain at least the correct name of the organ as the portion attribute value. Here, the paragraph can be detected, for example, regarding a space line or a line feed as a separator between paragraphs.

Next, the keyword attribute obtaining unit 107 associates the keyword selected in Step S201 with the attribute values obtained in Steps S203 to S205 (Step S206). For example, when the keyword "stain" is selected in Step S201 and the sentence including the keyword is "An early stain is recognized in the liver segment S1", "early phase", "existence", and "liver segment S1" are obtained as a phase attribute value, an existence attribute value, and a portion attribute value, respectively, in Steps S203 to S205. As a result, the keyword and attribute values are integrated into a combination of (Stain, Early phase, Existence, Liver segment S1).

Lastly, the keyword attribute obtaining unit 107 determines whether or not all the keywords obtained from the keyword extracting unit 106 is subject to Step S201. If the result is No, a return is made to Step S201, and if the result is Yes, the processing is completed (Step S207).

By performing Steps S201 to S206 in this way, it is possible to obtain the at least one combination of the keyword and the attribute values in Step S103.

Here, operations by the similar case searching apparatus 100 shown in FIG. 6 are further described.

The image feature extracting unit 108 extracts image feature quantities from the medical image group 20 obtained by the interpretation target obtaining unit 105, and outputs the extracted image feature quantities and the medical image group 20 to the search vector generating unit 109 (Step S104).

Next, the search vector generating unit 109 generates search vectors for the medical image group 20 using the combination of the keyword and the attribute value obtained from the keyword attribute obtaining unit 107, the image feature quantities obtained from the image feature extracting unit 108, and the relevance database 104, and outputs the search vectors to the similar case searching unit 110 (Step S105). More specifically, the search vector generating unit 109 obtains, from the relevance database 104, the degrees of relevance of the image feature quantities with the combination of the keyword and the attribute value obtained from the keyword attribute obtaining unit 107. The search vector generating unit 109 performs weighting on the image feature quantities obtained from the image feature extracting unit 108 by multiplying the image feature quantities with the obtained degrees of relevance as weights to the image feature quantities. For example, it is assumed that an average luminance value in the medical images, an average luminance value in central areas of the medical images, and an average luminance value in peripheral areas of the medical images are obtained as the image features in Step S104. At this time, the values of the obtained image feature quantities are presented as an image feature quantity vector (100, 50, 150). Likewise, degrees of relevance for an average luminance value in the medical images, an average luminance value in central areas of the medical images, and an average luminance value in peripheral areas of the medical images obtained from the relevance database 104 can be presented as a vector (0.8, 0.5, 0.2). In this case, the image features after weighting are obtained as (80, 25, 30) through the multiplication. In this way, the vector is generated as a search vector. It is to be noted that a search vector is generated for each of a first medical image group of first medical images in a case (a first case) which is an interpretation target and for each of second medical image groups of second medical images in a case (a second case) stored in the case database 101. Image feature quantities, keywords, and attribute values may be registered in advance in the case database 101, for the cases stored in the case database 101. In addition, the interpretation target obtaining unit 105 may obtain some of the cases registered in the case database 101, and the image feature extracting unit 108, the keyword extracting unit 106, and the keyword attribute obtaining unit 107 may perform extraction or obtainment processes.

Next, the similar case searching unit 110 searches out a second case having a high degree of similarity with the first case as the interpretation target, from among the cases stored in the case database 101, using the search vectors obtained from the search vector generating unit 109, and outputs the image interpretation report ID 22 of the searched-out second case to the output unit 111 (Step S106). A specific method for calculating degrees of similarity is to calculate, as the degrees of similarity, a cosine distance between the search vector for the first medical image group included in the first case obtained from the search vector generating unit 109 and the search vectors for the second medical image groups included in the second cases stored in the case database 101.

Lastly, the output unit 111 outputs, to an output-destination medium, case data corresponding to the image interpretation report ID 22 obtained from the similar case searching unit 110 (Step S107).

FIG. 8 is a diagram showing an example of a screen of the output-destination medium such as a liquid display which displays output from the output unit 111. As shown in FIG. 8, the output unit 111 presents similar cases in a descending order of degrees of similarity for a diagnosis by the image interpreter.

In addition, the output unit 111 may classify the cases searched out by the similar case searching unit 110 into case data item groups each based on similar diseases names, and display the respective case data item groups. FIG. 9 shows a classified version of the output example in FIG. 8, in which the search results are classified into the case data item groups each classified based on similar disease names and then displayed. The image interpreter needs to find out, using the results of searching the similar cases, disease name descriptions different from the diagnosis by himself or herself from the findings in the search results when considering a possibility of a disease other than the disease as the result of the diagnosis by himself or herself. By presenting a display screen for the respective case data item groups each classified based on similar disease names as the search results, the image interpreter can easily check the disease names in the cases presented as the search results. Therefore, it is possible to reduce image interpretation time.

Through Steps S101 to S107 shown in FIG. 6 executed as described above, the similar case searching apparatus 100 can search out the similar cases based on the viewpoint of the image interpreter for the result of the diagnosis in a userfriendly manner.

In addition, the interpretation target obtaining unit 105 does not always need to obtain a medical image group 20 and an image interpretation report 21 from the case database 101. For example, the interpretation target obtaining unit 105 may obtain, from another system, a medical image group 20 interpreted just before by the image interpreter and the image interpretation report thereof.

In addition, the similar case searching apparatus 100 may search the case database 101 for only case data items as search targets in each of which image findings 24 and a definitive diagnosis 25 match. The case database 101 includes the medical images based only on which it is impossible to indicate a lesion that matches the definitive diagnosis, due to image noise or characteristics of an imaging device. There is a high possibility that it is difficult to estimate a lesion based only on such medical images. Thus, presentation of such similar case data items may increase the risk of a misdiagnosis. In contrast, each of case data items in which image findings 24 and a definitive diagnosis 25 match is a case data item which guarantees that it is possible to point out the same lesion as the lesion in the definitive diagnosis from the medical images. Thus, the case data item is appropriate as a similar case data item. Thus, by determining, as the search targets, only the case data items in each of which image findings 24 and a definitive diagnosis 25 match, it is possible to reduce the risk of a misdiagnosis.

In addition, the case database 101, the keyword dictionary 102, the attribute dictionary 103, and the relevance database 104 may be included in the similar case searching apparatus 100.

In addition, the case database 101, the keyword dictionary 102, the attribute dictionary 103, and the relevance database 104 may be provided on a server connected to the similar case searching apparatus 100 via a network.

In addition, the image interpretation report 21 may be attached as supplemental data to the medical image group 20.

As described above, the similar case searching apparatus 100 according to this embodiment can search out the similar cases based on the viewpoint of the image interpreter for the result of the diagnosis by the image interpreter, even for the case in which the single image interpretation report is assigned to the plurality of medical images.

In other words, weighting is performed on the image feature quantities in the generation of the search vectors. At this time, the weights used in the weighting are the degrees of relevance between (i) the combination of the keyword and the attribute value of the keyword extracted from the image interpretation report included in the first case and (ii) the image feature quantities. The keyword and attribute value are values indicating the viewpoint of the image interpreter. For this reason, it is possible to search out the similar cases based on the viewpoint of the image interpreter. In addition, the attribute value indicates the supplemental concept of the keyword. For this reason, the attribute value is the clue for finding out the first medical image based on which the image interpretation report was written among the medical images in the first medical image group. With the clue, it is possible to search out the similar cases based on the viewpoint of the image interpreter even for the case in which the single text item is assigned to the medical images.

Embodiment 2

Next, a relevance database generating apparatus according to Embodiment 2 is described.

The relevance database generating apparatus in this embodiment has a feature of automatically generating a relevance database 104 from the case database 101.

The similar case searching apparatus 100 according to Embodiment 1 performs the similar case searching method using the relevance database 104 generated in advance. The relevance database 104 needs to be generated before use of the similar case searching apparatus 100.

The relevance database generating apparatus in this embodiment calculates degrees of relevance between (i) combinations of a keyword and attribute values thereof and (ii) image feature quantities, using medical images and a case data item obtained from the case database 101, and writes the calculated degrees of relevance to the relevance database 104.

In this way, the relevance database generating apparatus can automatically generate the relevance database 104 before use of the similar case searching apparatus 100.

With reference to FIG. 10 at first, structural elements of the relevance database generating apparatus are sequentially described below.

Embodiment 2

Explanation of Structure

FIG. 10 is a block diagram showing a functional structure of a relevance database generating apparatus according to Embodiment 2.

The elements in FIG. 10 which are the same as in those in FIG. 1 are assigned with the same reference signs, and the same descriptions are not repeated below. The relevance database generating apparatus 200 shown in FIG. 10 differs from the similar case searching apparatus 100 in the point of including an image feature attribute obtaining unit 201, a same attribute data generating unit 202, a relevance calculating unit 203, and a writing unit 204.

The image feature attribute obtaining unit 201 obtains attribute values corresponding to image feature quantities extracted by the image feature extracting unit 108, and outputs the obtained attribute values to the same attribute data generating unit 202. A specific attribute obtaining method is described later.

Next, the same attribute data generating unit 202 generates combinations of a keyword and image feature quantities both having an same attribute value, using the keyword and attribute value obtained from the keyword attribute obtaining unit 107 and the image features and attribute value obtained from the image feature attribute obtaining unit 201, and outputs the generated combinations to the relevance calculating unit 203.

Next, the relevance calculating unit 203 calculates degrees of relevance between the keyword and image features both having the same attribute value, using the combinations of the keyword and image features obtained from the same data generating unit. A specific relevance calculating method is described later.

Lastly, the writing unit 204 writes the degrees of relevance obtained from the relevance calculating unit 203 to the relevance database 104.

Next, descriptions are given of operations performed by the relevance database generating apparatus 200 configured as described above.

Embodiment 2

Explanation of Operations

Figure 11:
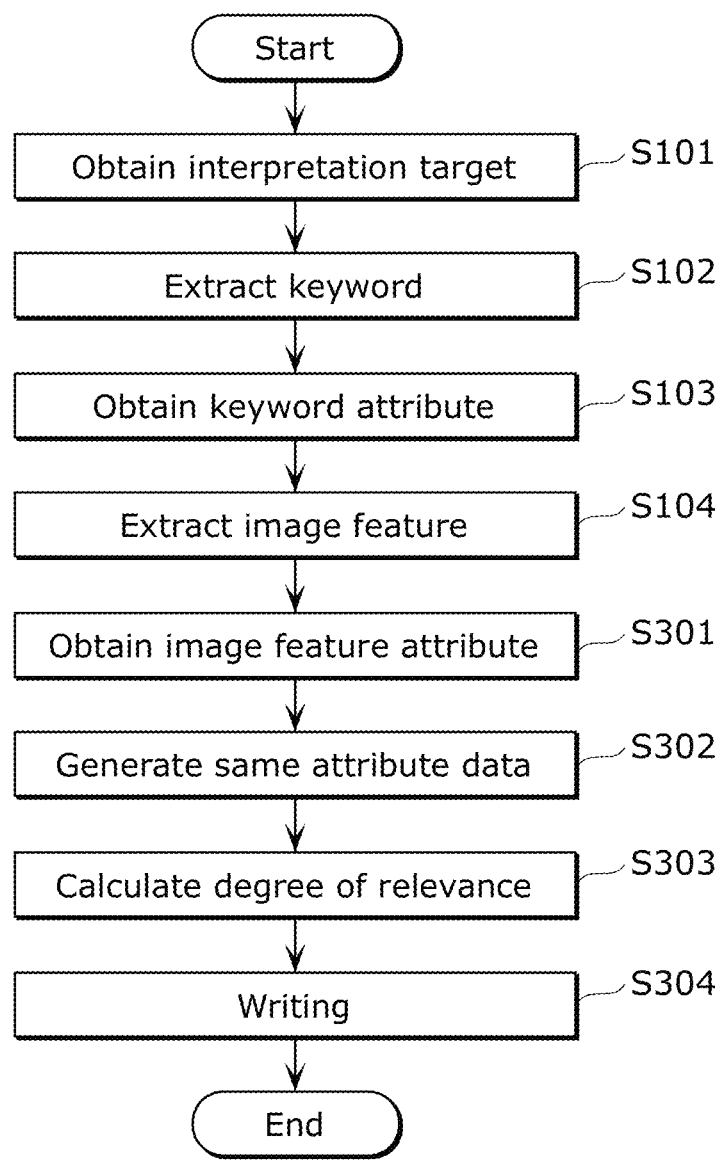
FIG. 11 is a flowchart of overall processes performed by the relevance database generating apparatus according to Embodiment 2.

FIG. 11 is a flowchart of overall processes performed by the relevance database generating apparatus 200. The processing in S101 to S104 is the same as in the processing in S101 to S104 shown in FIG. 6, and thus the same descriptions are not repeated below.

The image feature attribute obtaining unit 201 obtains the attribute values corresponding to the image feature quantities obtained from the image feature extracting unit 108, and outputs the obtained attribute values to the same attribute data generating unit 202 (Step S301). More specifically, the image feature attribute obtaining unit 201 obtains one or both of the time phase attribute value and the portion attribute value.

Figures 12, 13:
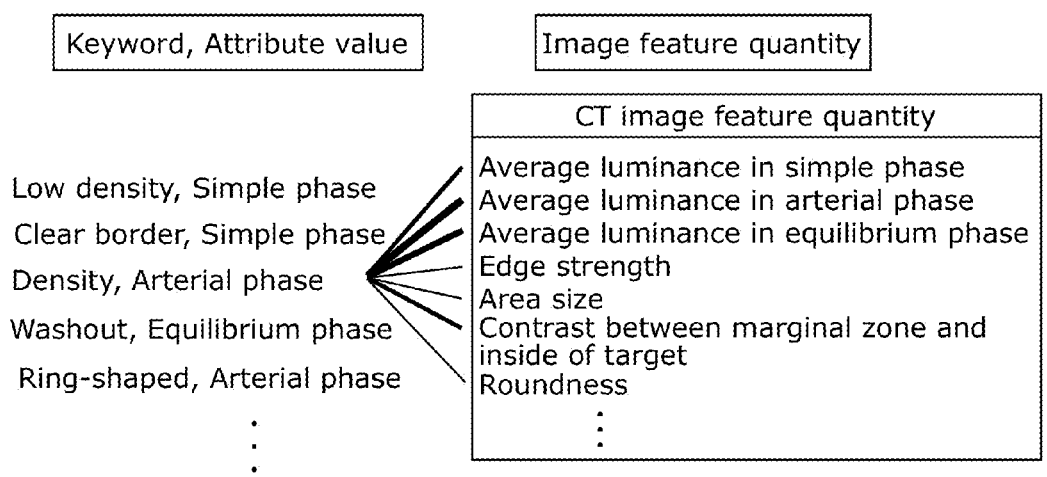
FIG. 12 is a diagram showing an example of a data table in which time phase attribute values and image capturing times are associated with each other.
FIG. 13 is a conceptual diagram of correlation ratios between a keyword and image feature quantities.

As shown in FIG. 12, a specific method for obtaining the time phase attribute value is to prepare in advance a data table in which image capturing times and time phase attribute values are associated with each other, and obtain the attribute values of the time phase attributes according to the image capturing times. In an example case, the time phase attribute value at the image capturing start time of an interpretation-target medical image is a "simple phase", and the time phase attribute value while another interpretation-target medical image is being captured from 1 to 80 seconds after the image capturing start time is an "arterial phase". In addition, in the case of a routine medical test such as a periodic medical check, it is also good to obtain time phase attribute values such as a "simple phase", an "arterial phase", and an "equilibrium phase", in accordance with the order of capturing the interpretation-target medical images. In addition, it is also possible to obtain time phase attribute values from image feature quantities such as luminance values of images of blood vessels.

In addition, it is possible to automatically obtain portion attribute values for the image feature quantities obtained from the image feature extracting unit 108 by performing, on the interpretation-target medical images from which image feature quantities are to be extracted, a particular image processing method for obtaining portion attribute values. The particular method is, for example, described in Non-patent Literature: "A method for extracting multi organs by estimating CT value distributions from four phase 3D abdominal CT images" by Sakashita, Deguchi, Kitasaka, Mori, and Suenaga, Technical Report of the Institute of Electronics, Information and Communication Engineers, medical images, Vol. 106, No. 145, pp. 49-54, July, 2006.

Next, the same attribute data generating unit 202 generates combinations of an image feature quantity and a keyword both having a common attribute value, using a combination of a keyword and an attribute value obtained from the keyword attribute obtaining unit 107 and combinations of an image feature quantity and an attribute value obtained by the image feature attribute obtaining unit 201. The same attribute data generating unit 202 outputs the generated combinations to the relevance calculating unit 203 (Step S302).

Next, the relevance calculating unit 203 calculates degrees of relevance between the image feature quantities and keyword, using the combinations obtained from the same attribute data generating unit 202, and outputs the calculated degrees of relevance to the writing unit 204 (Step S303). An exemplary method for calculating the degrees of relevance is to calculate the correlation ratios between the image feature quantities and the keyword. A method for calculating the correlation ratio between each of the image feature quantities and the keyword paired with each other is described in detail below.

The correlation ratio is an indicator indicating the correlation relationship between a qualitative data item and a quantitative data item, and is presented in Expression 1 below.

[Math. 1]

$$\eta^2 = \frac{\sum_i N_i(\bar{x}_i - \bar{x})^2}{\sum_i \sum_j (x_{ij} - \bar{x})^2} = \frac{S_B}{S_T}$$

(Expression 1)

Here, $x_{ij}$ is an i-th observed value that belongs to a category i of the qualitative data;

$\bar{x}_i$ denotes the average value of observed values that belong to the category i of the qualitative data;

$\bar{x}$ denotes the overall average value;

$N_i$ denotes the number of observations that belong to the category i;

$S_B$ denotes an inter-category dispersion; and $S_T$ denotes a total dispersion.

Image interpretation reports are classified into two categories based on the presence or absence of a certain keyword, and these categories are assumed to be qualitative data items. The raw values of image feature quantities of a kind extracted from the interpretation-target medical images are assumed to be qualitative data items. For example, for each of the cases included in the case database 101, the image interpretation reports are classified into the categories one of which includes image interpretation reports including a combination of the certain keyword and attribute value thereof and the other of which includes image interpretation reports without including such combination. Here, a description is given of an approach for calculating the correlation ratios between a keyword "Stain, Arterial phase" and an image feature quantity "Average luminance value inside a tumor, Arterial phase". It is to be noted here that the keyword and the image feature quantity are assigned with the common attribute value "Arterial phase". For this reason, calculating the correlation ratio between the keyword "Stain, Arterial phase" and the image feature quantity "Average luminance value inside a tumor, Arterial phase" is equivalent to calculating the correlation ratio between (i) the combination of the keyword "Stain" and the attribute value "Arterial phase" and (ii) the image feature quantity "Average luminance value inside a tumor". In Expression 1, it is assumed that the category i=1 includes the "Stain, Arterial phase", and that the category i=2 does not include the "Stain, Arterial phase". Here, x1j denotes the j-th observed value that is the "Average luminance value inside a tumor, Arterial phase" in the tumor image extracted from a case whose image interpretation report includes the "Stain, Arterial phase". Here, x2j denotes the j-th observed value that is the "Average luminance value inside a tumor, Arterial phase" in the tumor image extracted from a case whose image interpretation report does not include the "Stain, Arterial phase". The "Stain, Arterial phase" indicates that a CT value increases in the arterial phase in the contrast radiography, and thus the correlation ratio is expected to be increased (to a value close to 1) in this case. Furthermore, the stain depends on the type of the tumor, but does not depend on the size of the tumor, and thus the correlation between the keyword "Stain, Arterial phase" and an image feature quantity "Tumor size" is small (a value close to 0). In this way, the correlation ratios between all the pairs of a keyword and an image feature quantity are calculated.

FIG. 13 is a conceptual chart of correlation ratios between (i) the combination of the keyword and the attribute value and (ii) the image feature quantities. In this chart, the correlation ratios are shown in a multi-value representation in which the boldness of the solid lines corresponds to the magnitudes of the correlation rations. For example, the highest correlation is observed between the "Stain, Arterial phase" related to the arterial phase in which the CT value increases in the contrast radiography and the average luminance value (abbreviated as "Average luminance in arterial phase" in FIG. 13) inside the tumor in the arterial phase.

Focusing on these values of the correlation ratios makes it possible to identify the image feature quantities highly related to the combination of the certain keyword and the attribute value. In reality, it is highly likely that one case includes a plurality of lesions (tumors) and for which a plurality of images are captured. The image interpretation report of the case includes descriptions about the lesions. For example, in a contrast CT scan, CT images are captured at plural time points before and after the application of a contrast medium. For this reason, sets of slice images are obtained, each of the sets of slice images includes plural lesions (tumors), and a plurality of image feature quantities are extracted from each of the lesions. For this reason, the number of image feature quantities is obtained according to the Expression (the number of sets of slice images)×(the number of lesions detected from a patient)×(the number of kinds of image feature quantities). In addition, it is necessary to calculate the correlations between (i) the image feature quantities and (ii) the image interpretation items and the disease name extracted from the image interpretation report.

Up to this point, the method for calculating the correlation ratio between the keyword and each of the image feature quantities has been described.

Hereinafter, operations by the relevance database generating apparatus 200 shown in FIG. 11 are further described.

Lastly, the writing unit 204 writes the degrees of relevance obtained from the relevance calculating unit 203 to the relevance database 104 (Step S304).

As described above, the relevance database generating apparatus 200 according to this embodiment can calculate the degrees of relevance between the keyword and image feature quantities obtained from the case database 101, and thus can automatically generate the relevance database 104 before use by the similar case searching unit 100.

Figure 14:
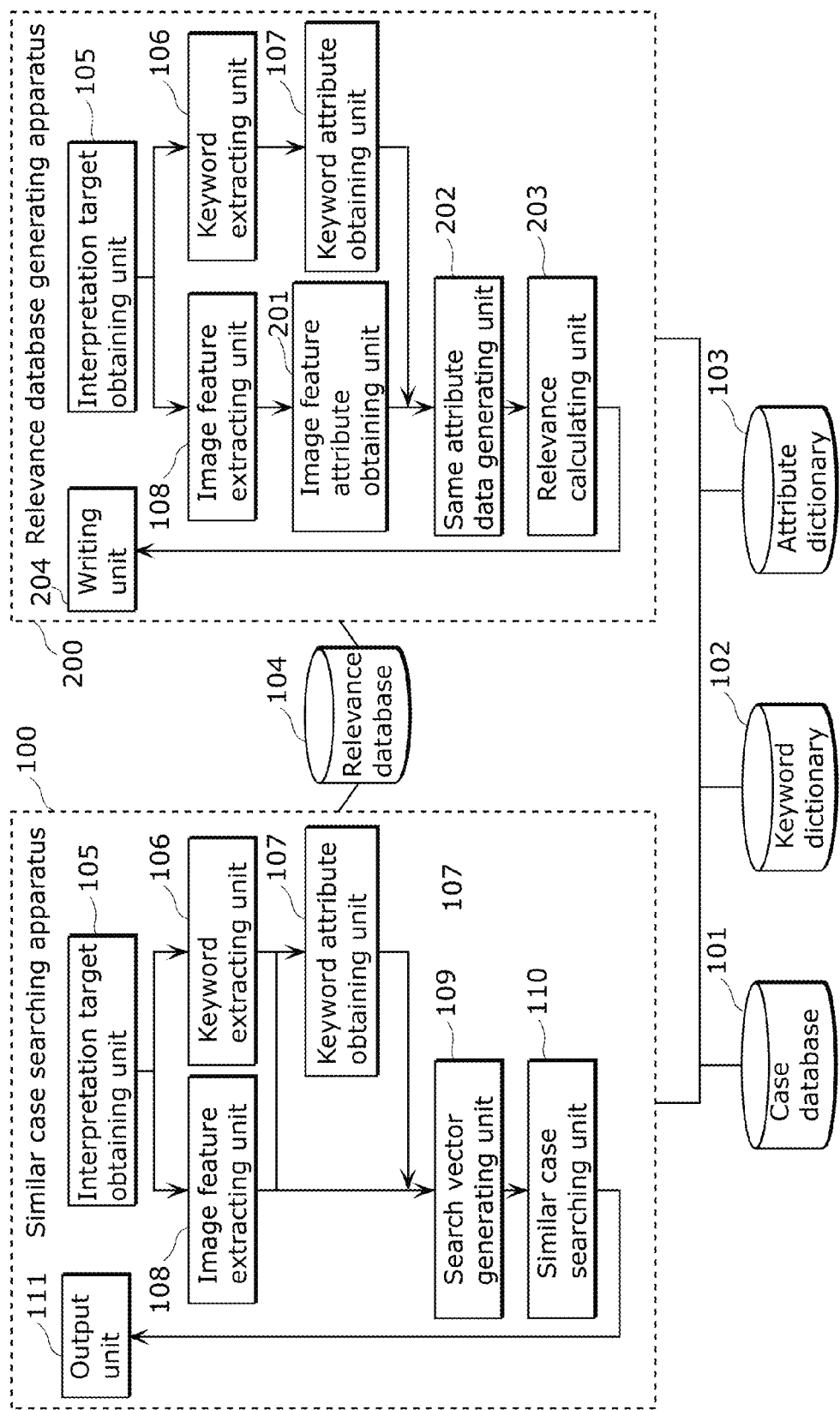
FIG. 14 is a diagram showing a relationship between the similar case searching apparatus according to Embodiment 1 and the relevance database generating apparatus according to Embodiment 2.

FIG. 14 shows the structural relationship between the similar case searching apparatus 100 according to Embodiment 1 and the relevance database generating unit 200 according to Embodiment 2. As shown in FIG. 14, the similar case searching apparatus 100 and the relevance database generating unit 200 are connected via the relevance database 104, the case database 101, the keyword dictionary 102, and the attribute dictionary 103.

Embodiment 3

Next, a relevance database generating apparatus according to Embodiment 3 is described.

The relevance database generating apparatus in this embodiment has a feature of automatically generating a relevance database 104 from a case database 101.

The relevance database generating apparatus 200 according to Embodiment 2 performs the automatic relevance calculating method when the case database 101 is provided. Here, the case database 101 is characterized in that diagnosis results are accumulated therein day by day to sequentially update the data stored therein. When an image interpretation report including a keyword which is not included in the relevance database 104 is newly added to the case database 101, the degree of relevance for the newly added keyword has not yet been calculated. For this reason, it is impossible to perform any search using the keyword. This causes a problem that the similar case searching apparatus 100 cannot search out similar cases based on a viewpoint of an image interpreter.

To solve this problem, the relevance database generating apparatus according to this embodiment calculates the degrees of relevance between the combination of the new keyword and an attribute value thereof and image feature quantities, in response to the update in the case database 101, and writes the calculation results to the relevance database 104.

In this way, even when the case database 101 is updated, it is possible to search out the similar cases based on the viewpoint of the image interpreter.

Figure 15:
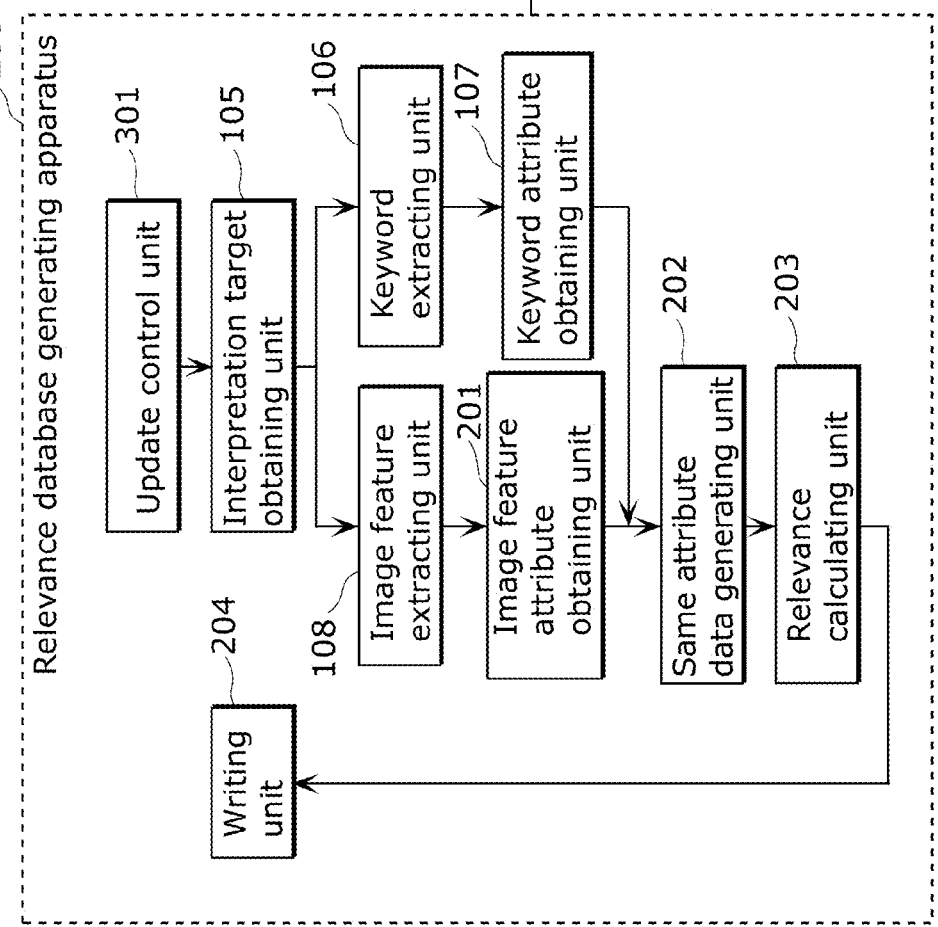
FIG. 15 is a block diagram showing a functional structure of a relevance database generating apparatus according to Embodiment 3.

With reference to FIG. 15 at first, structural elements of the relevance database generating apparatus are sequentially described below.

Embodiment 3

Explanation of Structure

FIG. 15 is a block diagram showing a functional structure of a relevance database generating apparatus according to Embodiment 3.

The elements in FIG. 15 which are the same as in those in FIG. 10 are assigned with the same reference signs, and the same descriptions are not repeated below. The relevance database generating apparatus 300 shown in FIG. 15 differs from the relevance database generating apparatus 200 shown in FIG. 10 in the point of including an update control unit 301 which determines whether or not to update the relevance database 104 based on a case obtained from the case database 101.

The update control unit 301 determines whether or not to update the relevance database 104 using the medical images and the case data item obtained from the case database 101. The update control unit 301 updates the relevance database 104 when the answer is Yes. When the answer is No, the update control unit 301 does not update the relevance database 104. A specific determining method is described later. When determining the update of the relevance database 104, the update control unit 301 causes an interpretation target obtaining unit 105 to obtain the case data item from the case database 101.

Next, descriptions are given of operations performed by the relevance database generating apparatus 300 configured as described above.

Embodiment 3

Explanation of Operations

Figure 16:
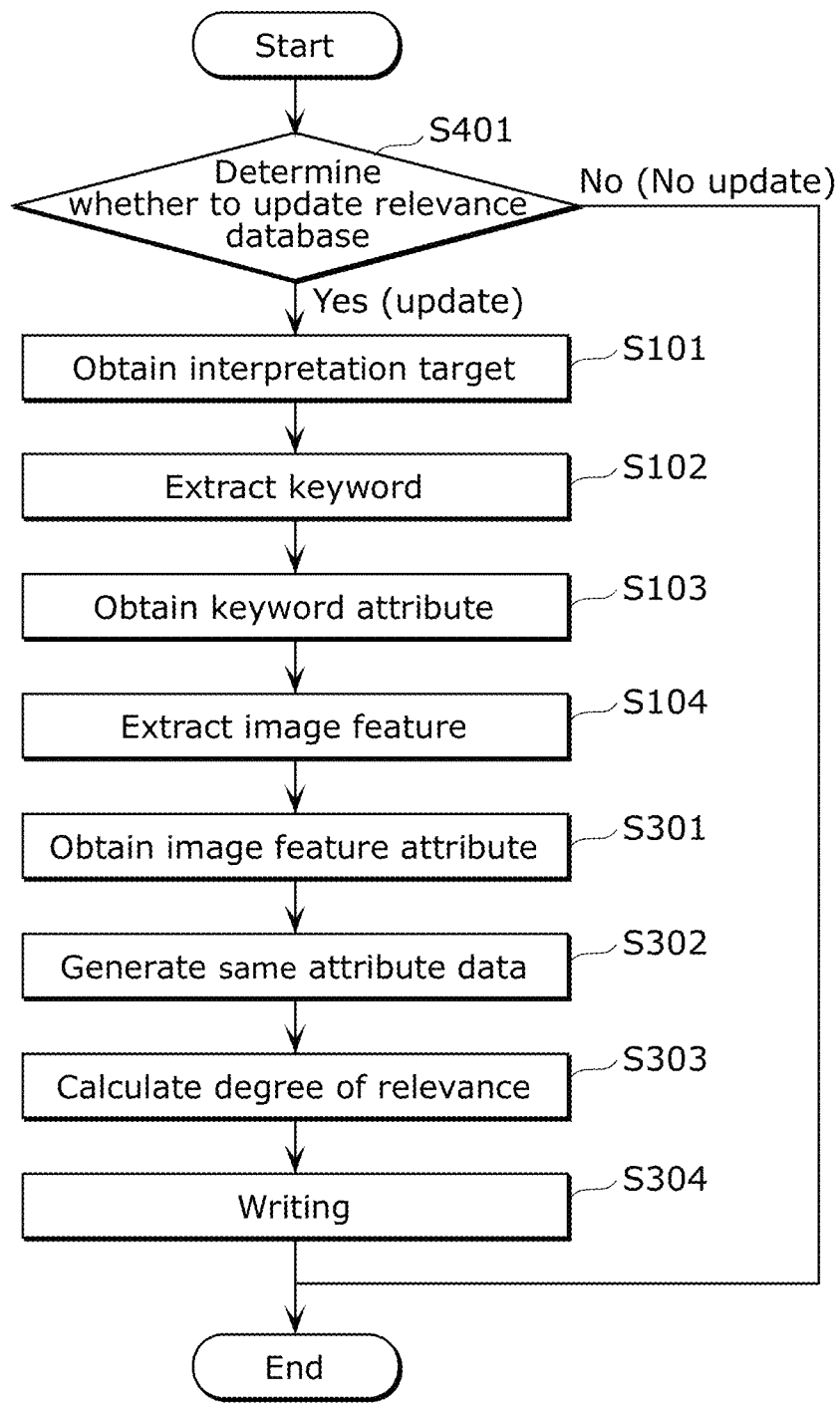
FIG. 16 is a flowchart of overall processes performed by a relevance database generating apparatus according to Embodiment 3.

FIG. 16 is a flowchart of overall processes performed by the relevance database generating apparatus 300. The elements in FIG. 16 which are the same as in those in FIG. 11 are assigned with the same reference signs, and the same descriptions are not repeated below.

The update control unit 301 determines whether or not to update the relevance database 104 using the case obtained from the case database 101. The processing advances to Step S101 when the answer is Yes, and otherwise, the processing is completed (Step S401).

As an exemplary specific update determining method, it is good to sequentially update the relevance database 104 each time the case database 101 is updated. In other words, when the case database 101 is updated, the update control unit 301 causes the interpretation target obtaining unit 105 to obtain a plurality of medical images and image interpretation reports included in all the case data items included in the case database 101.

In addition, as another exemplary update determining method, it is also good to count up the appearance frequency of each of keywords included in the case database 101, and update the relevance database 104 when update is made for a keyword having an appearance frequency that is no more than a threshold value among the keywords in the case database 101. In other words, the update control unit 301 causes the interpretation target obtaining unit 105 to obtain, at the time of update of the case database 101, one or more image interpretation reports each including a keyword having an appearance frequency no more than the threshold value among all the image interpretation reports and medical images corresponding to the one or more image interpretation reports stored in the case database 101. The relevance database 104 stores the degrees of relevance of the respective keywords. When a keyword included in the case database 101 has a sufficiently large appearance frequency, the degree of relevance of the keyword has already been calculated using a sufficient number of data items. If a keyword having a high appearance frequency is newly added and the appearance frequency is re-calculated, the value does not change so much, and thus the necessity of updating the degree of relevance is low. In the opposite case of a keyword having a low appearance frequency, the degree of relevance is highly likely to be inaccurate, and thus the necessity of updating the degree of relevance is high. In this way, by determining whether or not update is allowed according to the appearance frequency of the keyword in the case database, it is possible to reduce the calculation amount at the time of update, and to thereby reduce the update time.

As described above, the relevance database generating apparatus 300 according to this embodiment can update the degrees of relevance of a keyword and image feature quantities even when the case database 101 is updated, and can search out similar cases based on a viewpoint of the image interpreter.

Although the case searching apparatus and relevance database generating apparatus according to embodiments of the present disclosure have been described above, these embodiments are non-limiting exemplary embodiments. Those skilled in the art will readily appreciate that many modifications are possible in the exemplary embodiment and other embodiments are possible by arbitrarily combining the structural elements of the embodiment with others without materially departing from the novel teachings and advantages in the present disclosure. Accordingly, all such modifications are intended to be included within the scope of the present disclosure.

In the aforementioned similar case searching apparatus 100, the keyword attribute obtaining unit 107 extracts attribute values based on keywords extracted from image interpretation reports. However, when it is impossible to extract attribute values based on keywords, it is also good to obtain attribute values from medical images auxiliarily. The obtainment of these attribute values is performed in the same manner as the obtainment of attribute values by the image feature attribute obtaining unit 201 of the relevance database generating apparatus 200. The search vector generating unit 109 generates search vectors using the attribute values obtained from the medical images instead of attribute values which are otherwise obtained by the keyword attribute obtaining unit 107, and the similar case searching unit 110 searches out similar cases using the generated search vectors.

The aforementioned similar case searching apparatus or any one of the relevance database generating apparatuses may be configured as a computer system including a microprocessor, a Read Only Memory (ROM), a Random Access Memory (RAM), a hard disk drive, a display unit, a keyboard, a mouse, and so on. The RAM or hard disk drive stores a computer program. The similar case searching apparatus or the relevance database generating apparatus attains its functions through the microprocessor's operations according to the computer program. Here, the computer program is configured to combine a plurality of instruction codes for giving instructions to the computer for allow the computer to attain its functions.

Figure 17:
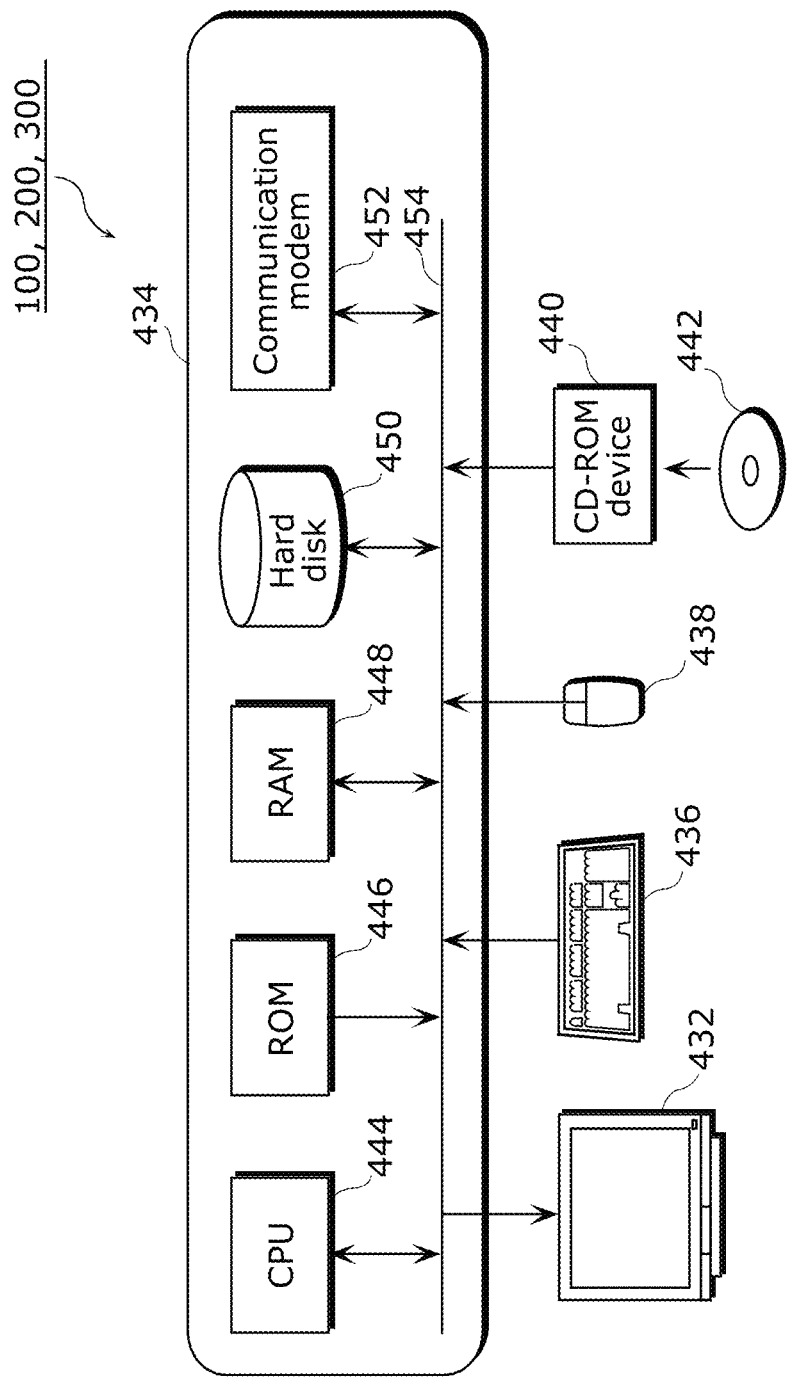
FIG. 17 is a block diagram showing a hardware structure of a computer system which includes either the similar case searching apparatus according to Embodiment 1 or the relevance database generating apparatus according to Embodiment 2 or 3.

FIG. 17 is a block diagram showing a hardware structure of a computer system which includes either the similar case searching apparatus according to Embodiment 1 or the relevance database generating apparatus according to Embodiments 2 or 3.

The similar case searching apparatus or the similar case searching apparatus includes: a computer 434; a keyboard 436 and a mouse 438 for giving instructions to the computer 434; a display 432 for presenting information such as a result of computation by the computer 434; and a CD-ROM device 440 and a communication modem (not shown) for reading the program to be executed by the computer 434.

The program performed by either the similar case searching apparatus or the relevance database generating apparatus is recorded onto a CD-ROM 442 which is a computer-readable recording medium, and is read by a CD-ROM device 440. Alternatively, the program is read by a communication modem 452 via a computer network.

The computer 434 includes: a Central Processing Unit (CPU) 444; a ROM 446; a RAM 448; a hard disk 450; a communication modem 452; and a bus 454.

The CPU 444 executes the program read through the CD-ROM device 440 or the communication modem 452. The ROM 446 stores the program or data necessary for operations by the computer 434. The RAM 448 stores data such as parameters at the time of the execution of the program. The hard disk 450 stores the program or data, etc. The communication modem 452 communicates with other computers via a computer network. The bus 454 establishes mutual connections of the CPU 444, the ROM 446, the RAM 448, the hard disk 450, the communication modem 452, the display 432, the keyboard 436, the mouse 438, and the CD-ROM device 440.

Furthermore, some or all of the structural elements of the similar case searching apparatus or the relevance database generating apparatus may be configured with a single system Large Scale Integration (LSI). The system LSI is a super-multi-function LSI manufactured by integrating structural units on a single chip, and is specifically a computer system configured to include a microprocessor, a ROM, a RAM, and so on. The RAM stores a computer program. The system LSI achieves its function through the microprocessor's operations according to the computer program.

Furthermore, some or all of the structural elements constituting the similar case searching apparatus or the relevance database generating apparatus may be configured as an IC card which can be attached to and detached from the similar case searching apparatus or the relevance database generating apparatus, or as a stand-alone module. The IC card or the module is a computer system composed of a microprocessor, a ROM, a RAM and so on. The IC card or the module may include the aforementioned super-multi-function LSI. The IC card or the module achieves its function through the microprocessor's operations according to the computer program. The IC card or the module may also be implemented to be tamper-resistant.

In addition, an embodiment of the present disclosure may be any one of the methods described above. In addition, the present disclosure may be realized as a computer program for causing a computer to execute the above-described method, or as a digital signal of the computer program.

Furthermore, an embodiment of the present disclosure may be realized as a non-transitory computer-readable recording medium having the computer program or the digital signal recorded thereon. Examples of the recording medium include a flexible disc, a hard disk, a CD-ROM, an MO, a DVD, a DVD-ROM, a DVD-RAM, a BD (Blu-ray (registered trademark) Disc), and a semiconductor memory. In addition, the present disclosure may be realized as the digital signal recorded on the non-transitory computer-readable recording medium.

Furthermore, an embodiment of the present disclosure may be realized as the aforementioned computer program or digital signal transmitted via a telecommunication line, a wireless or wired communication line, a network represented by the Internet, a data broadcast, and so on.

In addition, an embodiment of the present invention may be a computer system including a microprocessor and a memory. The memory may store the program and the microprocessor may operates according to the computer program.

Furthermore, it is also possible to execute another independent computer system by transmitting the program or the digital signal recorded on the aforementioned non-transitory computer-readable recording media, or by transmitting the program or digital signal via the aforementioned network and the like.

Each of the structural elements in each of the above-described embodiments may be configured in the form of an exclusive hardware product, or may be realized by executing a software program suitable for the structural element. Each of the structural elements may be realized by means of a program executing unit, such as a CPU and a processor, reading and executing the software program recorded on a recording medium such as a hard disk or a semiconductor memory.

Here, the software program for realizing a similar case searching method according to each of the embodiments is a program described below.

The program causes a computer to execute the similar case searching method for searching out, from a case database, a second case data item similar to a first case data item including a first medical image group of first medical images and a first image interpretation report which is a text data item indicating a result of interpreting the first medical image group, the similar case searching method being executed by a computer and including: extracting a plurality of image feature quantities from the first medical image group; extracting a keyword from the first image interpretation report, the keyword being either (a) an image interpretation item which is a character string indicating a feature of at least one of the first medical images or (b) a disease name which is a result of a diagnosis made by a user based on the first medical images; obtaining an attribute value which is a word indicating a supplemental concept of the keyword, from a sentence including the keyword extracted in the extracting; with reference to a relevance database storing the degrees of relevance between (i) a combination of the keyword extracted in the extracting and the attribute value of the keyword obtained in the obtaining and (ii) the respective image feature quantities extracted in the extracting, performing weighting on (i) the image feature quantities extracted in the extracting and (ii) image feature quantities extracted from a second medical image group of second medical images included in the at least one second case data item stored in the case database, using the degrees of relevance as weights; and generating a search vector for the first medical image group and a search vector for the second medical image group, each of the search vectors having, as elements, corresponding ones of image feature quantities resulting from the weighting; and searching out the at least one second case data item stored in the case database, based on a degree of similarity between the search vector for the first medical image group and the search vector for the second medical group.

Here, the software program for realizing a relevance database generating method according to each of the embodiments is a program described below.

The program causes a computer to execute the relevance database generating method, including: extracting image feature quantities from a plurality of medical images; obtaining attribute values of the respective image feature quantities extracted in the extracting, from the plurality of medical images; extracting, as a keyword, either an image interpretation item or a disease name, from an image interpretation report which is a text data item describing a result of interpretation of the medical images by a user, the image interpretation item being a character string indicating a feature of at least one of the medical images, and the disease name being a result of a diagnosis made by the user based on the medical images; obtaining an attribute value of the keyword, from a sentence including the keyword extracted in the extracting; generating a combination of the keyword and each of image feature quantities both having a same attribute value, based on (i) the keyword and the attribute value of the keyword extracted from the image interpretation report and (ii) the image feature quantities extracted from the medical images and the attribute values of the respective image feature quantities; and calculating, from the combination of the keyword and each of the image feature quantities both having the same attribute value, a degree of relevance between the keyword and the image feature quantity, and generating a relevance database indicating a degree of relevance between (i) the combination of the keyword and the attribute value of the keyword and (ii) the image feature quantity.

INDUSTRIAL APPLICABILITY

The present disclosure is applicable to a similar case searching apparatus or the like which outputs similar cases for diagnosis results by image interpreters. In addition, the present disclosure is applicable as a relevance database generating apparatus or the like which generates relevance database for use by the similar case searching apparatus.

The invention claimed is:

1. A similar case searching apparatus which searches out, from a case database, at least one second case data item similar to a first case data item including a first medical image group of first medical images and a first image interpretation report which is a text data item indicating a result of interpreting the first medical image group, the similar case searching apparatus comprising:
  a microprocessor; and
  a non-transitory memory having stored thereon executable instructions, which when executed by the microprocessor, cause the similar case searching apparatus to function as:
  an image feature extracting unit configured to extract a plurality of image feature quantities from the first medical image group;
  a keyword extracting unit configured to extract a keyword from the first image interpretation report, the keyword being either (a) an image interpretation item which is a character string indicating a feature of at least one of the first medical images or (b) a disease name which is a result of a diagnosis made by a user based on the first medical images;
  a keyword attribute obtaining unit configured to (i) search for a plurality of attribute values, the attribute values including a time phase attribute value, an existence attribute value, and a portion attribute value, and (ii) obtain at least one of the attribute values which is a word indicating a supplemental concept of the keyword, from a sentence including the keyword extracted by the keyword extracting unit;

a search vector generating unit configured to:

with reference to a relevance database storing the degrees of relevance between (i) a combination of the keyword extracted by the keyword extracting unit and the at least one attribute value of the keyword obtained by the keyword attribute obtaining unit and (ii) the respective image feature quantities extracted by the image feature extracting unit, perform weighting on (i) the image feature quantities extracted by the image feature extracting unit and (ii) image feature quantities extracted from a second medical image group of second medical images included in the at least one second case data item stored in the case database, using the degrees of relevance as weights; and generate a search vector for the first medical image group and a search vector for the second medical image group, each of the search vectors having, as elements, corresponding ones of image feature quantities resulting from the weighting; and a similar case searching unit configured to search out the at least one second case data item stored in the case database, based on a degree of similarity between the search vector for the first medical image group and the search vector for the second medical group.

2. The similar case searching apparatus according to claim 1, wherein the time phase attribute value indicates a relative image capturing time of a corresponding one of the first medical images in the first medical image group or a relative image capturing time period in which the corresponding first medical image is captured, from the sentence including the keyword extracted by the keyword extracting unit.

3. The similar case searching apparatus according to claim 1, wherein the existence attribute value indicates existence or non-existence of information in the at least one of the first medical images, from the sentence including the keyword indicating the information and extracted by the keyword extracting unit.

4. The similar case searching apparatus according to claim 1, wherein the portion attribute value indicates a portion of an organ whose image is to be interpreted, from the sentence including the keyword extracted by the keyword extracting unit.

5. The similar case searching apparatus according to claim 1, wherein the executable instructions, when executed by the microprocessor, cause the similar case searching apparatus to further function as an output unit configured to output the at least one second case data item searched out by the similar case searching unit to outside the similar case searching apparatus.

6. The similar case searching apparatus according to claim 5, wherein the output unit is configured to classify each of the at least one second case data item searched out by the similar case searching unit into a corresponding one of case data item groups each based on similar diseases names, and output the classified at least one second case data item to outside the similar case searching apparatus.

7. The similar case searching apparatus according to claim 1, wherein the similar case searching unit is configured to search for only one or more second case data items each assigned with an image interpretation report in which an image finding and a definitive diagnosis match from among second case data items stored in the case database, the image finding is a result of a diagnosis made by an image interpreter based on the second medical image group included in the second case data item, and the definitive diagnosis is a final diagnosis result obtained based on the second medical image group included in the second case data item.

8. A relevance database generating apparatus, comprising:

a microprocessor; and a non-transitory memory having stored thereon executable instructions, which when executed by the microprocessor, cause the relevance database generating apparatus to function as:

an image feature extracting unit configured to extract image feature quantities from a plurality of medical images;

an image feature attribute obtaining unit configured to obtain attribute values of the respective image feature quantities extracted by the image feature extracting unit, from the plurality of medical images;

a keyword extracting unit configured to extract, as a keyword, either an image interpretation item or a disease name, from an image interpretation report which is a text data item describing a result of interpretation of the medical images by a user, the image interpretation item being a character string indicating a feature of at least one of the medical images, and the disease name being a result of a diagnosis made by the user based on the medical images;

a keyword attribute obtaining unit configured to (i) search for a plurality of attribute values of the keyword, the attribute values including a time phase attribute value, an existence attribute value, and a portion attribute value, and (ii) obtain at least one of the attribute values of the keyword, from a sentence including the keyword extracted by the keyword extracting unit;

a same attribute data generating unit configured to generate a combination of the keyword and each of image feature quantities both having a same attribute value, based on (i) the keyword and the at least one attribute value of the keyword extracted from the image interpretation report and (ii) the image feature quantities extracted from the medical images and the attribute values of the respective image feature quantities; and a relevance calculating unit configured to calculate, from the combination of the keyword and each of the image feature quantities both having the same attribute value, a degree of relevance between the keyword and the image feature quantity, and generate a relevance database indicating a degree of relevance between (i) the combination of the keyword and the at least one attribute value of the keyword and (ii) the image feature quantity.

9. The relevance database generating apparatus according to claim 8, wherein the time phase attribute value indicates a relative image capturing time of a corresponding one of the medical images or a relative image capturing time period in which the corresponding medical image is captured, from the sentence including the keyword extracted by the keyword extracting unit.

10. The relevance database generating apparatus according to claim 8,
wherein the existence attribute value indicates existence or non-existence of information shown by the keyword, from the sentence including the keyword, the keyword indicating the feature of the at least one of the medical images and extracted by the keyword extracting unit.

11. The relevance database generating apparatus according to claim 8,
wherein the portion attribute value indicates a portion of an organ whose image is to be interpreted, from the sentence including the keyword extracted by the keyword extracting unit.

12. The relevance database generating apparatus according to claim 8,
wherein the image feature attribute obtaining unit is configured to obtain time phase attribute values as the attribute values of the respective image feature quantities extracted by the image feature extracting unit, from image capturing times of the respective medical images, with reference to a data table in which the image capturing times of the medical images and the time phase attribute values are associated with each other.

13. The relevance database generating apparatus according to claim 8,
wherein the executable instructions, when executed by the microprocessor, cause the relevance database generating searching apparatus to further function as:
an interpretation target obtaining unit configured to obtain a plurality of medical images and an image interpolation report corresponding to the medical images included in a case data item, from a case database storing the case data item; and
an update control unit configured to cause the interpretation target obtaining unit to obtain, at the time of update of the case database, the medical images and the image interpretation report stored in the case database,
wherein the image feature extracting unit is configured to extract image feature quantities from the medical images obtained by the interpretation target obtaining unit, and
the keyword extracting unit is configured to extract the keyword from the image interpretation report obtained by the interpretation target obtaining unit.

14. The relevance database generating apparatus according to claim 13,
wherein the update control unit is configured to cause the interpretation target obtaining unit to obtain, at the time of the update of the case database, medical images and image interpretation reports included in all case data items included in the case database.

15. The relevance database generating apparatus according to claim 13,
wherein the update control unit is configured to cause the interpretation target obtaining unit to obtain, at the time of the update of the case database, (i) one or more image interpretation reports each including a keyword having an appearance frequency no more than a threshold value among all image interpretation reports stored in the case database and (ii) medical images corresponding to the one or more image interpretation reports.

16. A similar case searching method for searching out, from a case database, a second case data item similar to a first case data item including a first medical image group of first medical images and a first image interpretation report which is a text data item indicating a result of interpreting the first medical image group, the similar case searching method being executed by a computer and comprising:
extracting a plurality of image feature quantities from the first medical image group;
extracting a keyword from the first image interpretation report, the keyword being either (a) an image interpretation item which is a character string indicating a feature of at least one of the first medical images or (b) a disease name which is a result of a diagnosis made by a user based on the first medical images;
searching for a plurality of attribute values, the attribute values including a time phase attribute value, an existence attribute value, and a portion attribute value;
obtaining at least one of the attribute values which is a word indicating a supplemental concept of the keyword, from a sentence including the keyword extracted in the extracting;
with reference to a relevance database storing the degrees of relevance between (i) a combination of the keyword extracted in the extracting and the at least one attribute value of the keyword obtained in the obtaining and (ii) the respective image feature quantities extracted in the extracting,
performing weighting on (i) the image feature quantities extracted in the extracting and (ii) image feature quantities extracted from a second medical image group of second medical images included in the at least one second case data item stored in the case database, using the degrees of relevance as weights; and
generating a search vector for the first medical image group and a search vector for the second medical image group, each of the search vectors having, as elements, corresponding ones of image feature quantities resulting from the weighting; and
searching out the at least one second case data item stored in the case database, based on a degree of similarity between the search vector for the first medical image group and the search vector for the second medical image group.

17. A relevance database generating method, comprising:
extracting image feature quantities from a plurality of medical images;
obtaining attribute values of the respective image feature quantities extracted in the extracting, from the plurality of medical images;
extracting, as a keyword, either an image interpretation item or a disease name, from an image interpretation report which is a text data item describing a result of interpretation of the medical images by a user, the image interpretation item being a character string indicating a feature of at least one of the medical images, and the disease name being a result of a diagnosis made by the user based on the medical images;
searching for a plurality of attribute values of the keyword, the attribute values including a time phase attribute value, an existence attribute value, and a portion attribute value;
obtaining at least one of the attribute values of the keyword, from a sentence including the keyword extracted in the extracting;
generating a combination of the keyword and each of image feature quantities both having a same attribute value, based on (i) the keyword and the at least one attribute value of the keyword extracted from the image interpretation report and (ii) the image feature quantities extracted from the medical images and the attribute values of the respective image feature quantities; and calculating, from the combination of the keyword and each of the image feature quantities both having the same attribute value, a degree of relevance between the keyword and the image feature quantity, and generating a relevance database indicating a degree of relevance between (i) the combination of the keyword and the at least one attribute value of the keyword and (ii) the image feature quantity.

18. A non-transitory computer-readable recording medium storing a program for causing a computer to execute the similar case searching method according to claim 16.

19. A non-transitory computer-readable recording medium storing a program for causing a computer to execute the relevance database generating method according to claim 17.

* * * * *